(12) United States Patent
Nichols

(10) Patent No.: US 12,251,852 B2
(45) Date of Patent: Mar. 18, 2025

(54) SPALTED WOOD PRODUCTS AND DEVICES, SYSTEMS, COMPOSITIONS, AND METHODS FOR PRODUCTION

(71) Applicant: Vermont Wildwoods, Marshfield, VT (US)

(72) Inventor: Parker Nichols, Burlington, VT (US)

(73) Assignee: Vermont Wildwoods, Marshfield, VT (US)

( * ) Notice: Subject to any disclaimer, the term of this patent is extended or adjusted under 35 U.S.C. 154(b) by 0 days.

(21) Appl. No.: 18/507,534

(22) Filed: Nov. 13, 2023

(65) Prior Publication Data

US 2024/0157595 A1 May 16, 2024

Related U.S. Application Data

(60) Provisional application No. 63/383,466, filed on Nov. 11, 2022.

(51) Int. Cl.
*B27K 5/02* (2006.01)

(52) U.S. Cl.
CPC ..................... *B27K 5/02* (2013.01)

(58) Field of Classification Search
CPC ....................................... B27K 5/02
See application file for complete search history.

(56) References Cited

U.S. PATENT DOCUMENTS

| | | |
|---|---|---|
| 4,346,175 A | 8/1982 | Enfors et al. |
| 4,698,305 A | 10/1987 | Hansson |
| 5,518,921 A | 5/1996 | Blanchette et al. |
| 8,399,075 B2 | 3/2013 | Beakler |
| 10,479,906 B2 | 11/2019 | Robinson et al. |
| 2013/0153114 A1 | 6/2013 | Beakler |
| 2015/0033480 A1 | 2/2015 | Yang et al. |

FOREIGN PATENT DOCUMENTS

| | | | |
|---|---|---|---|
| CN | 103497897 B | 2/2016 | |
| CN | 103182726 A | 11/2016 | |
| ES | 2689962 | * 11/2018 | ............ B27K 3/002 |

OTHER PUBLICATIONS

Andrew Hilton; Spatting, A Fungus Amongus; http://hiltonhandcraft.com/Articles/Spalting-a-Fungus-Amongus.asp; pp. 1-11, Pub Date for this web site article Mar. 12, 2007.*
Alan Lacer; Spalted Wood; http://www.alanlacer.com/articles/spalting.html; pp. 1-5, Pub Date this web site article Mar. 8, 2007.*
Producing Spalted Wood; USDA Forest Service; Mar. 2004; pp. 1-2; MO-1; Madison, WI.*
WOOD Magazine Staff, Make it special with spalted wood. https://www.woodmagazine.com/wood-supplies/wood-figure/make-it-special-with-spalted-wood, Dec. 30, 2020.*
Hugh Morris, et al; "The dark side of fungal competition and resource capture in wood: Zone line spalting from science to application"; Materials & DesignVolume 201, Mar. 2021, 109480; https://www.sciencedirect.com/science/article/pii/S0264127521000332.
Sara C. Robinson, et al.; "Methods of inoculating Acer spp., *Populus tremuloides*, and *Fagus grandifolia* logs for commercial spalting applications"; Journal of Wood Science; 59, pp. 351-357 (2013); https://jwoodscience.springeropen.com/articles/10.1007/s10086-013-1335-5.

* cited by examiner

*Primary Examiner* — Amina S Khan
(74) *Attorney, Agent, or Firm* — GIBRALTAR CONSULTING LLC; Tariq S. Najee-Ullah

(57) ABSTRACT

The disclosure provides for artificially produced spalted wood products and devices, systems, compositions, and methods for production. A spalt inoculum mixture that includes a fungal component is developed and incubated with a hardwood substrate under controlled conditions to generate naturally modified produced spalted wood from the hardwood substrate. The devices, systems, and methods increase the reliability and reproducibility of spalted wood production on a commercial scale.

10 Claims, 18 Drawing Sheets

Wood Chip Inoculum
1. Harvest 6 ft³ forest topsoil
2. Mix in 1 ft³ spalt inoculumA
3. Incubate 2-3 months at 5-15°C
4. Monitor fungal development
5. Add 2700 ft³ mill residueB
6. Combine using a front loader

Hardwood Substrate
1. Winter cut ~200 maple logs
2. Fungi colonize at forest site
3. Sporulation on log ends ~2 days
4. Select grade 2 veneer logs
5. Transport logs to aging site

Aging Site Preparation
1. Select a level site ~ 100 x 40 ft.
2. Clear organic 'O' surface soil
3. Remove 'A' horizon soil ~1 ft. D
4. Lay 6" of wood chip inoculum
5. Stack 10 ft. cut logs 100L x 3D x 3H
6. Overlay with 6" inoculum

SPALTED WOOD PRODUCTS AND DEVICES, SYSTEMS, COMPOSITIONS, AND METHODS FOR PRODUCTION

PRIORITY CLAIM

This application is a U.S. Non-Provisional Utility Application entitled, "SPALTED WOOD PRODUCTS AND DEVICES, SYSTEMS, COMPOSITIONS, AND METHODS FOR PRODUCTION" which claims priority to U.S. Provisional Application No. 63/383,466 filed Nov. 11, 2022 entitled, "SPALTED WOOD PRODUCTS AND DEVICES, SYSTEMS, COMPOSITIONS, AND METHODS FOR PRODUCTION" the entirety of which is hereby incorporated by reference as if fully set forth herein.

FIELD

The disclosure relates to approaches for reliable and reproducible production of spalted wood products on a commercial scale. A spalt inoculum mixture that includes a fungal component is developed and incubated with a hardwood substrate under controlled conditions to generate spalted wood from the hardwood substrate. The approaches disclosed increase the robustness and reproducibility of spalted wood production and enable these activities to be effectively carried out on a commercial scale.

BACKGROUND

Spalted wood is sought after for use in carpentry and design due to its aesthetic and visually appealing characteristics. Currently, spalted wood occurs naturally in some forest ecosystems due to the presence of certain spalting fungi which completely degrade wood, including fallen trees and decaying logs, and produce a characteristic spalted pattern on at least the surface of the wood. To use the spalted wood in industry, lumber prospectors must search for naturally occurring spalted wood within forests, identify viable specimens, and transport the specimens for further handling, processing, storage, and sale.

Naturally occurring spalted wood is produced by nature unreliably and in small quantities, and production takes significant time. The timeframe for natural spalted wood production can range from about 3 years to about 20 years in a wild hardwood forest, and frequency of occurrence can range from about 1.68% to about 5%, meaning that most natural wood that may be a suitable substrate for spalting goes unspalted. Additionally, the wood that becomes spalted is spalted very slowly over long periods of time. The result of these natural inefficiencies is that the demand for spalted wood is not being met.

In addition, a portion of spalted wood that is produced naturally is structurally unsound due to fungi degrading the wood substrate being colonized by very aggressive primary decomposers. These aggressive primary decomposers render the wood structurally unsound due to the aggressiveness of their decomposition. This degrades the wood at a depth of the wood below the surface or may otherwise not be uniformly degraded by the fungi.

These shortcomings limit the usefulness of harvested naturally occurring spalted wood specimens. For example, structurally compromised spalted wood specimens cannot be milled into veneer. These occurrences further limit the supply of spalted wood products, despite the demand. Others have attempted to apply various fungi or fungi extracts directly onto wood substrates or veneers with limited success and at a small scale.

Accordingly, there is a need for improved devices, systems, and methods for reliable and reproducible production of spalted wood products in a commercial setting that increases the availability of spalted wood for carpentry, design projects including interior design, and other applications. The present invention addresses this unmet need.

SUMMARY

Generally, the disclosure provides devices and systems, as well as compositions and methods, for reliably producing spalted wood products at commercial scale. The devices and systems include incubators, sensors, and monitoring and control systems, as well as general-purpose lumber operation devices and hardware, and the compositions and methods include and utilize fungi-based compositions that have markedly different characteristics compared to any naturally occurring counterpart and that can be used to effectively produce spalted wood products.

In one aspect, the disclosure provides a moisture and temperature-controlled device, which may be referred to as an "aging chamber", that is configured for inducing indoor spalting. In one or more instances, for example, when outdoor space and/or availability of wood chips or spalting medium is limited, the aging chamber may be utilized. The aging chamber device may be relatively large and includes an overhead sliding track door and is dark (i.e., a light-limited environment) with one or more access doors built onto a radiant heated concrete floor slab with an added amount of B-horizon soil, for example. The chamber may also contain a commercial scale refrigeration system with a carbon dioxide ($CO_2$) and temperature sensor built in.

Methods of producing spalted wood products that utilize the aging chamber device use a combination of fungal isolates and wood chips and may utilize appropriate sensors and monitoring and control systems, e.g., computer systems. The chamber may be insulated, ventilated, and used for inducing spalted wood from logs or industry standard packets of variable, fungally inoculated sawn lumber.

In another aspect, the disclosure provides compositions and methods for inducing spalting in wood specimens to produce spalted wood products, either outdoors or indoors. A method for producing a spalted wood product includes applying a wood chip inoculum with a mature fungal component to a wood specimen to produce a fungal-wood mixture and aging the fungal-wood mixture at an aging site for a certain aging period to produce the spalted wood product. Methods for harvesting and preparing the wood specimen, preparing the wood chip inoculum, and monitoring and controlling the aging process are also provided.

In yet another aspect, the disclosure provides spalted wood products, such as veneer products, produced at least in part by methods of the disclosure. The spalted wood products may be more competitively produced and may be more economically viable from a business perspective, such that the demand for these products can be satisfied.

The invention generally relates to devices, systems, compositions, and spalted wood products which may be manufactured with appropriate materials and processes, and which may be scaled as needed.

In another aspect, the system includes a commercial-scale, methods, and conditions for establishing controlled, outdoor, and indoor, incubation environments to reliably induce decorative spalt line patterns of hardwood species using a specified combination of fungal isolates, hardwood chips, supplemental irrigation and select hardwood species. As a result, the timeframe of producing spalted timber is reduced to 12-18 months as compared to about 3 years to about 20 years for wild, forest-produced wood to decay. Additionally, as a result of implementations of this system, the frequency of fungi-induced spalted logs has increased to >90% from the 1.68% to about 5% frequency recovered in wild hardwood forests. Further, the structural integrity of spalted wood product derived from implementations of this system is superior to and uniform compared to wild-crafted wood spalt. Implementations of this system overcomes the time and scarcity limitations of natural-sought, forest-produced spalted wood by providing a steady, reliable source of product within a comparatively short timeframe.

Other objects, features, and advantages of the invention will become apparent from the following detailed description taken in conjunction with the accompanying drawings.

BRIEF DESCRIPTION OF THE DRAWINGS

Although the characteristic features of the invention will be particularly pointed out in the claims, the invention itself and manners in which it may be made and used may be better understood after a review of the following description, taken in connection with the accompanying drawings, wherein like numeral annotations are provided throughout.

FIGS. 16A and 16B show a flowchart of the example method for producing the spalted wood product, according to the present disclosure.

DETAILED DESCRIPTION OF THE INVENTION

Figure 1:
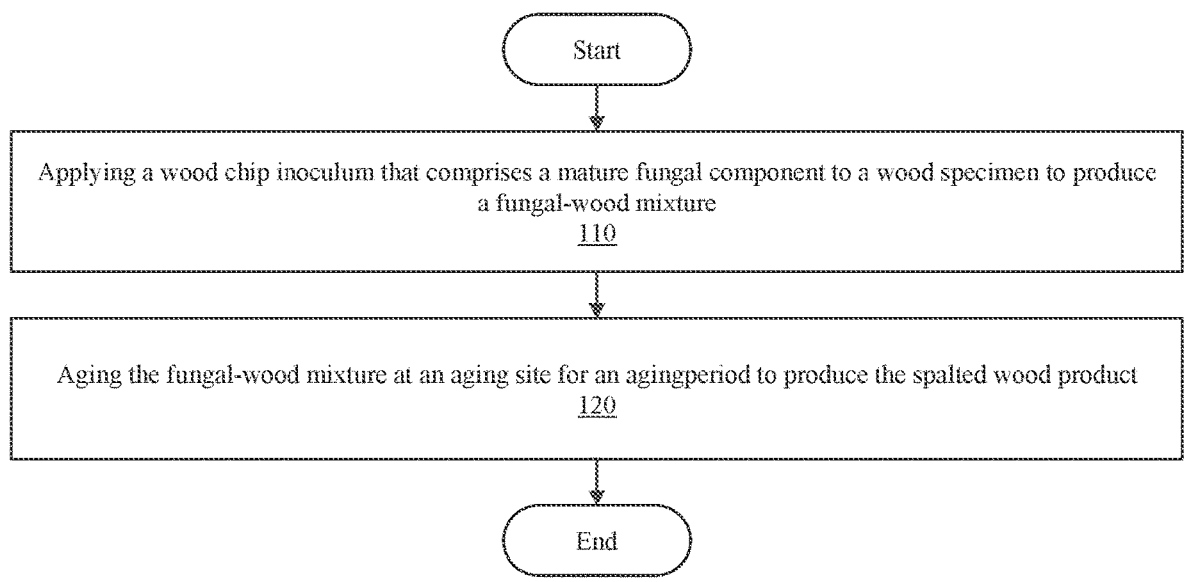
FIG. 1 is a flowchart illustrating a method for producing a spalted wood product, according to some embodiments of the present disclosure.

Reference is made herein to the attached drawings. Like reference numerals may be used in the drawings to indicate like or similar elements of the description. The figures are intended for representative purposes and should not be considered limiting.

The present disclosure can be understood more readily by reference to the following detailed description of the present disclosure and the examples included therein.

Before the present articles, systems, devices, and/or methods are disclosed and described, it is to be understood that they are not limited to specific implementations unless otherwise specified, or to particular approaches unless otherwise specified, as such can, of course, vary. It is also to be understood that the terminology used herein is for the purpose of describing aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited.

FIG. 1 is a flowchart that describes a method for producing a spalted wood product, according to some embodiments of the present disclosure. In some embodiments, at 110, the method may include applying a wood chip inoculum that comprises a mature fungal component to a wood specimen to produce a fungal-wood mixture. At 120, the method may include aging the fungal-wood mixture at an aging site for an aging period to produce the spalted wood product. In some embodiments, the wood specimen may comprise a basswood specimen, a beech specimen, a poplar specimen, a sugar maple specimen, and/or a yellow birch specimen.

In some embodiments, the wood chip inoculum further comprises a new woodchip and inoculated woodchip mature spalt inoculum component and a mill residue component that may be comprised of an approximately 3:1 ratio of debarked healthy maple chips to spalted sawdust and/or spalted edge waste and/or spalted bark. In some embodiments, the composition may include a mature spalt inoculum component comprising aged spalt inoculum.

Figure 2:
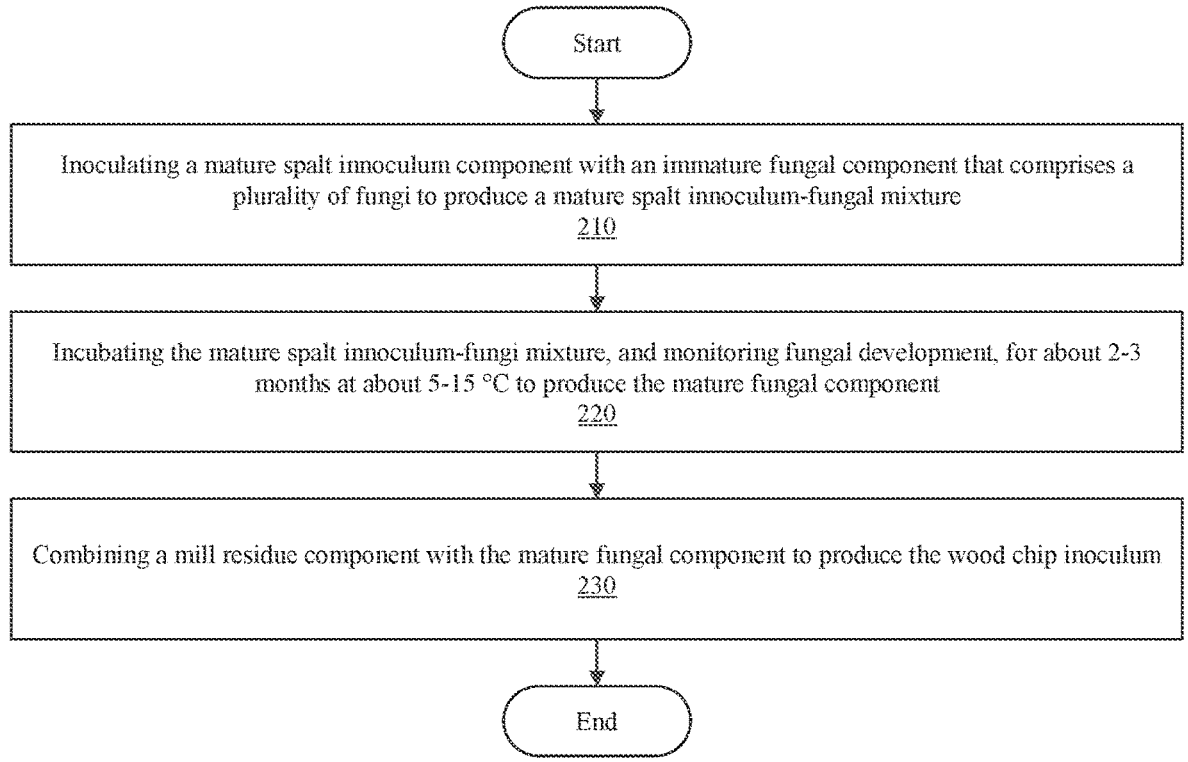
FIG. 2 is a flowchart further illustrating the method for producing a spalted wood product from FIG. 1, according to some embodiments of the present disclosure.

FIG. 2 is a flowchart that further describes the method for producing a spalted wood product from FIG. 1, according to some embodiments of the present disclosure. In some embodiments, the wood chip inoculum may be produced by, the method may include at block 210, inoculating a mature spalt inoculum component with an immature fungal component that comprises a plurality of fungi to produce a mature spalt inoculum-fungal mixture. At block 220, incubating the mature spalt inoculum-fungi mixture, and monitoring fungal development, for about 2-3 months at about 5-15° C. to produce the mature fungal component. At block 230, combining a mill residue component with the mature fungal component to produce the wood chip inoculum.

In an embodiment, different spalting fungi mixes may be used that would stain the woods blue or red instead of creating zone lines. The process has been reproducible for maple, ash and beech logs or lumber with fungal combinations to induce spalting. The size of outdoor or indoor environments and amounts of logs or lumber may be scaled up or down to achieve spalting.

Figure 3:
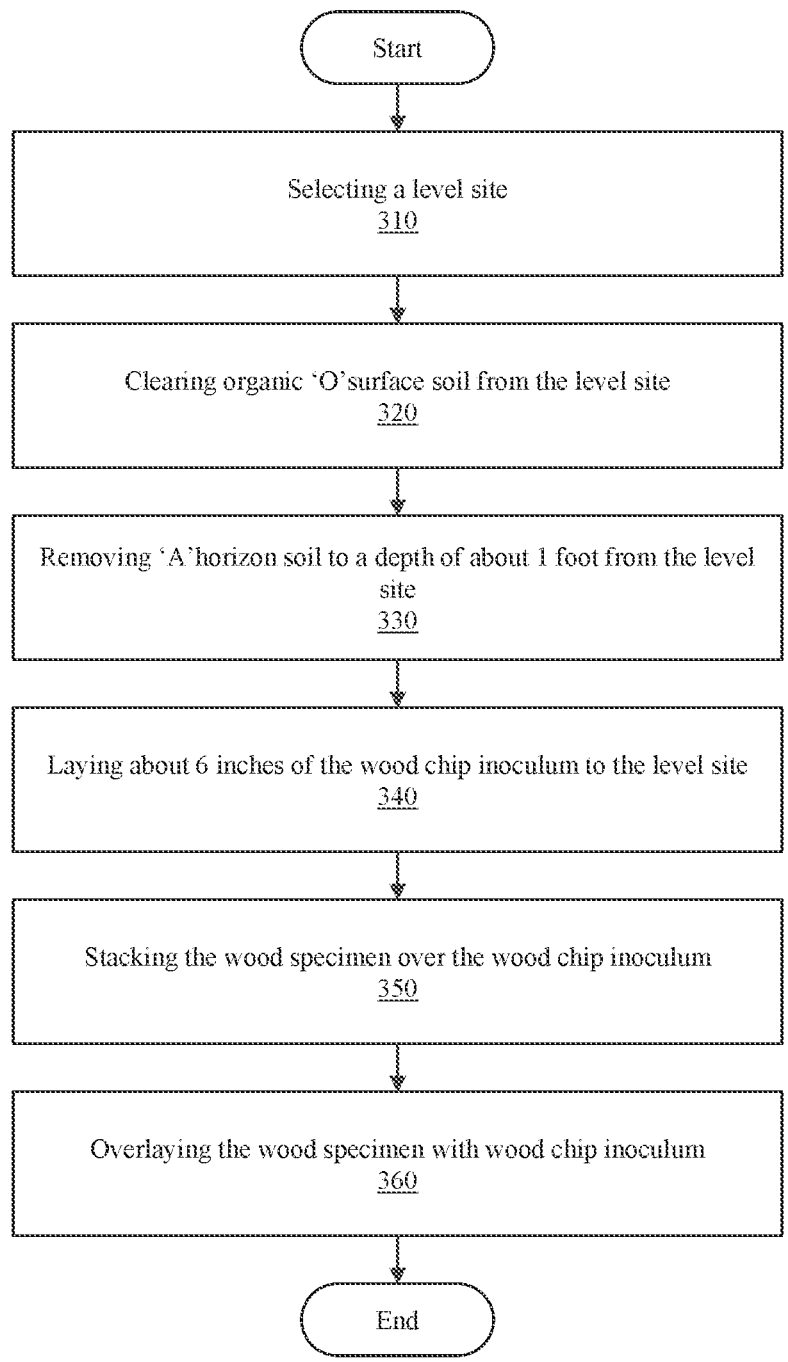
FIG. 3 is a flowchart further illustrating the method for producing a spalted wood product from FIG. 1, according to some embodiments of the present disclosure.

FIG. 3 is a flowchart that further describes the method for producing a spalted wood product from FIG. 1, according to some embodiments of the present disclosure. In some embodiments, the aging site may be prepared by, the method may include 310 to 360. At block 310, selecting a level site. At block 320, clearing organic 'O' surface soil from the level site, for example. At block 330, removing 'A' horizon soil to a depth of about 1 foot from the level site. At block 340, laying about 6 inches of the wood chip inoculum to the level site. At block 350, stacking the wood specimen over the wood chip inoculum. At block 360, overlaying the wood specimen with wood chip inoculum.

Figure 4:
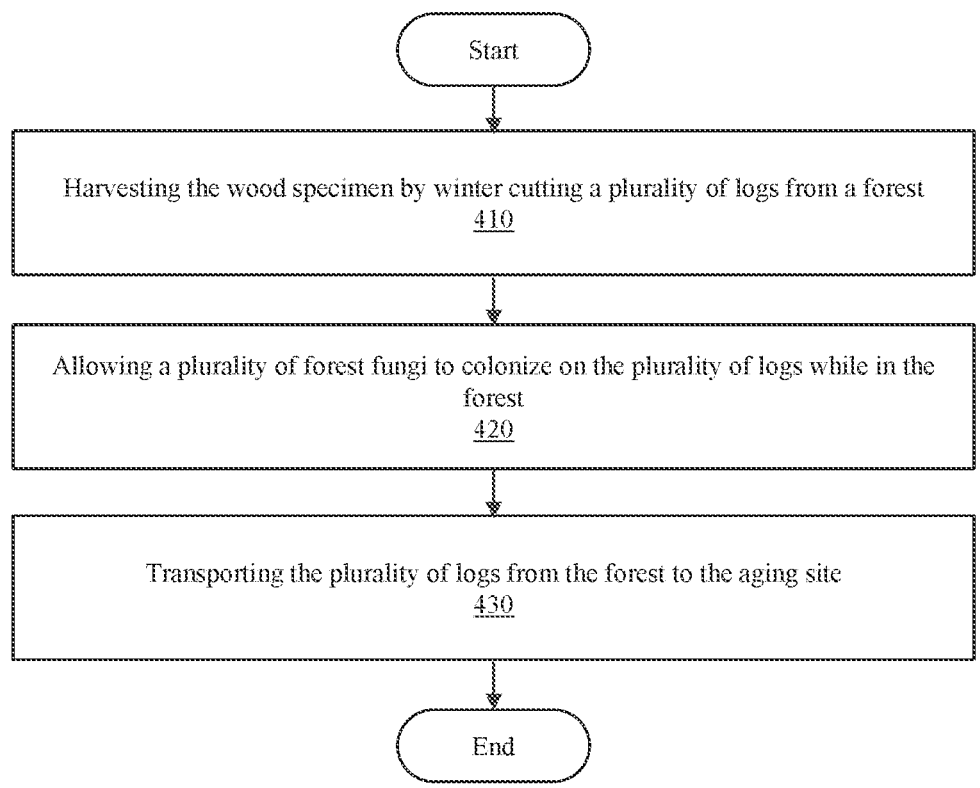
FIG. 4 is a flowchart further illustrating the method for producing a spalted wood product from FIG. 1, according to some embodiments of the present disclosure.

FIG. 4 is a flowchart that further describes the method for producing a spalted wood product from FIG. 1, according to some embodiments of the present disclosure. In some embodiments, the method may include harvesting the wood specimen by performing the steps at block 410, in which winter cutting a plurality of logs from a forest is performed. At block 420, the harvesting may include allowing a plurality of forest fungi to colonize on the plurality of logs while in the forest. At block 430, the harvesting may include transporting the plurality of logs from the forest to the aging site.

Figure 5:
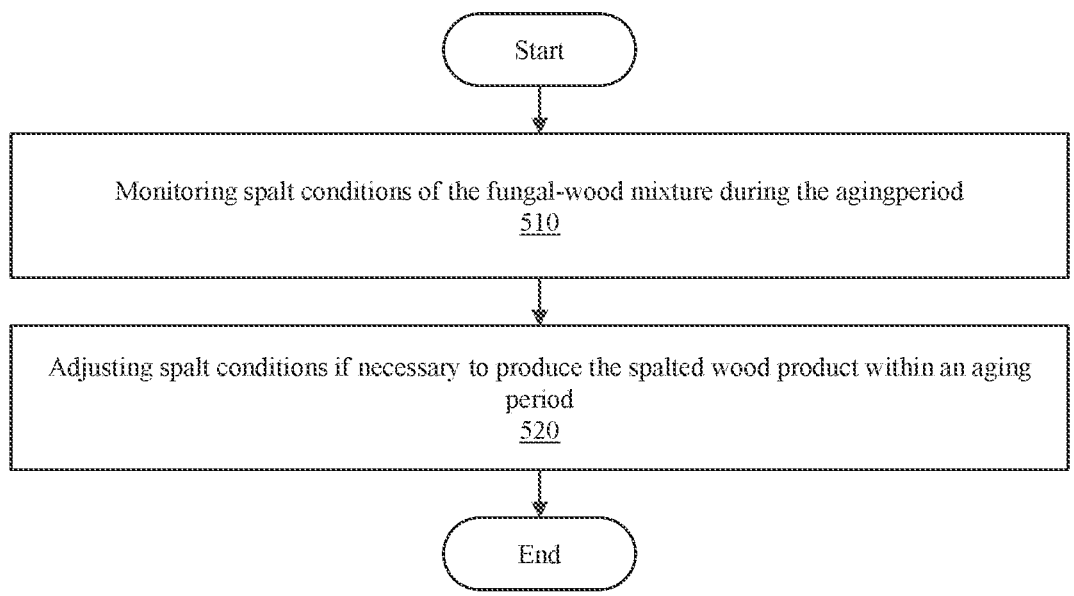
FIG. 5 is a flowchart further illustrating the method for producing a spalted wood product from FIG. 1, according to some embodiments of the present disclosure.

FIG. 5 is a flowchart that further describes the method for producing a spalted wood product from FIG. 1, according to some embodiments of the present disclosure. In some embodiments, at 510, the method may include monitoring spalt conditions of the fungal-wood mixture during the aging period. At 520, the method may include adjusting spalt conditions if necessary to produce the spalted wood product within an aging period. In some embodiments, spalt conditions may include about 40% moisture and a temperature that may be less than about 15° C.

Figure 6A:
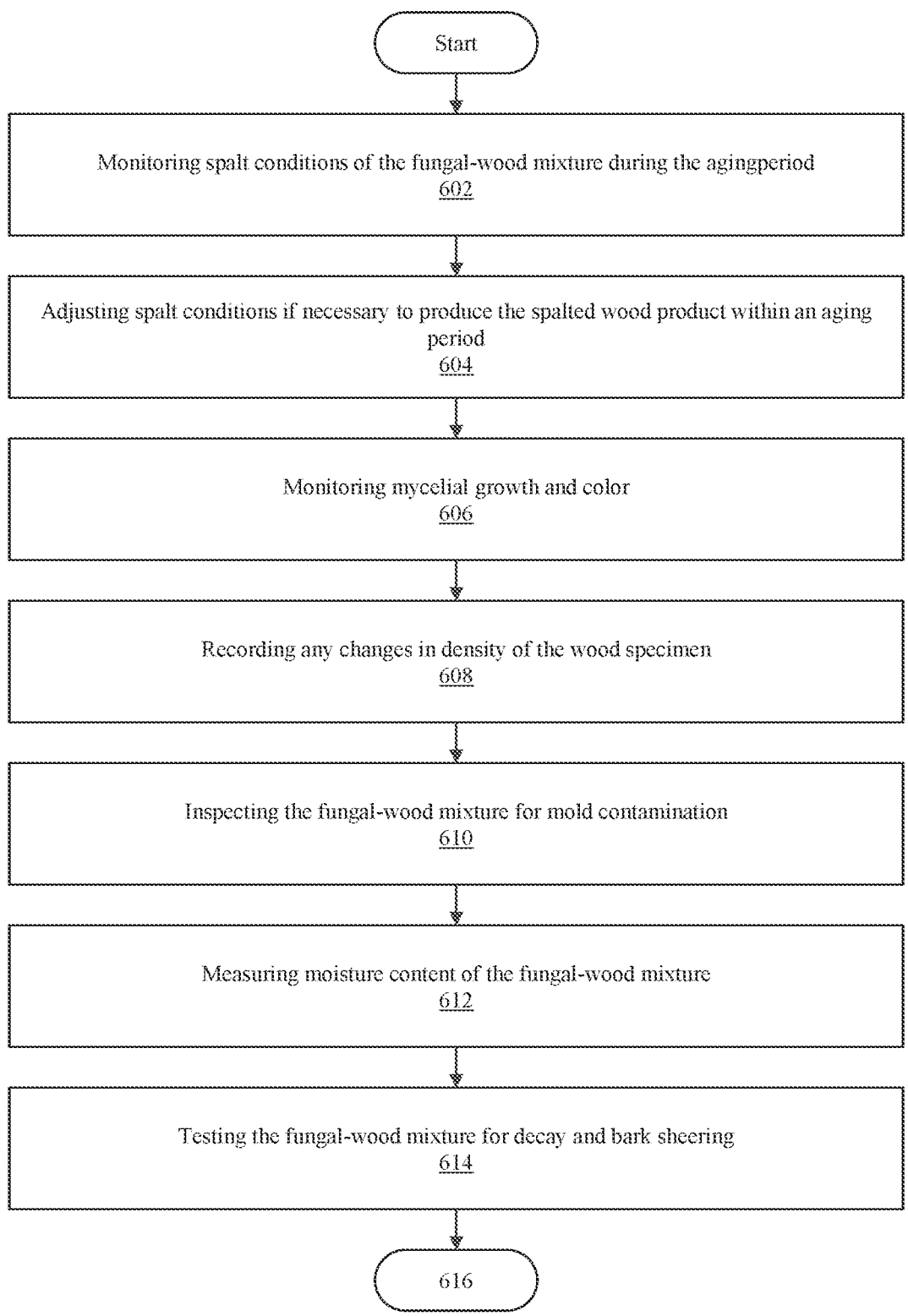
FIG. 6A is a flowchart further illustrating the method for producing a spalted wood product from FIG. 1, according to some embodiments of the present disclosure.
Figure 6B:
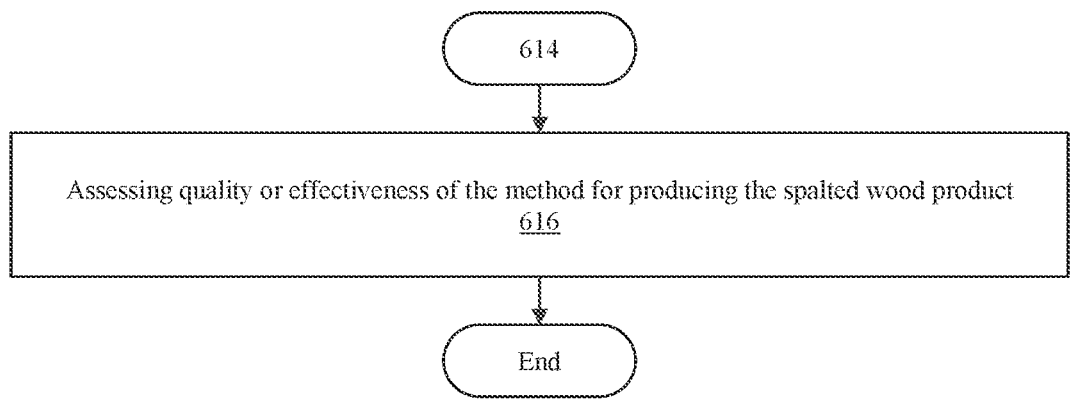
FIG. 6B is a flowchart extending from FIG. 6A and further illustrating the method for producing a spalted wood product, according to some embodiments of the present disclosure.

FIGS. 6A to 6B are flowcharts that further describe the method for producing a spalted wood product from FIG. 1, according to some embodiments of the present disclosure. In some embodiments, at 510, the method may include monitoring spalt conditions of the fungal-wood mixture during the aging period. At 520, the method may include adjusting spalt conditions if necessary to produce the spalted wood product within an aging period. In some embodiments, monitoring spalt conditions comprises, the method may include 602 to 616. At block 602, monitoring spalt conditions of the fungal-wood mixture during the aging period. At block 604, adjusting spalt conditions if necessary to produce the spalted wood product within an aging period. At block 606, monitoring mycelial growth and color. At block 608, recording any changes in density of the wood specimen. At block 610, inspecting the fungal-wood mixture for mold contamination. At block 612, measuring moisture content of the fungal-wood mixture. At block 614, testing the fungal-wood mixture for decay and bark sheering. At block 616, assessing quality or effectiveness of the method for producing the spalted wood product.

Figure 7:
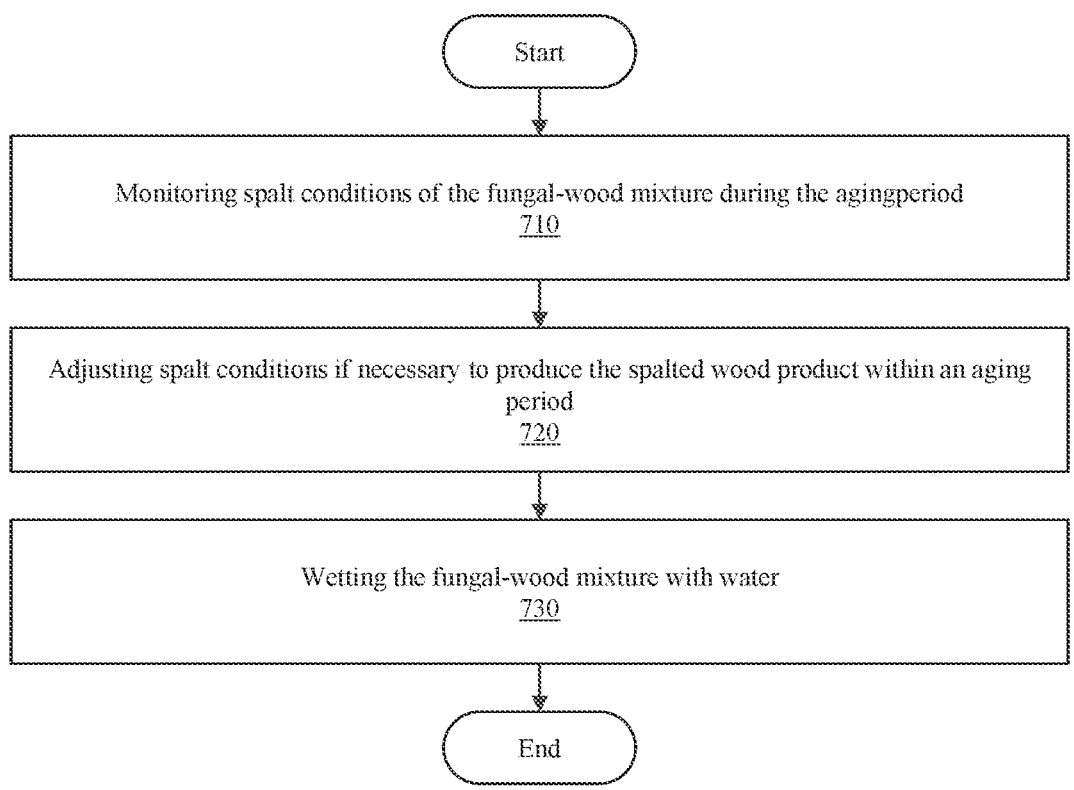
FIG. 7 is a flowchart further illustrating the method for producing a spalted wood product from FIG. 1, according to some embodiments of the present disclosure.

FIG. 7 is a flowchart that further describes the method for producing a spalted wood product from FIG. 1, according to some embodiments of the present disclosure. In some embodiments, at 510, the method may include monitoring spalt conditions of the fungal-wood mixture during the aging period. At 520, the method may include adjusting spalt conditions if necessary to produce the spalted wood product within an aging period. In some embodiments, at block 710, monitoring spalt conditions of the fungal-wood mixture during the aging period. At block 720, adjusting spalt conditions if necessary to produce the spalted wood product within an aging period. At block 730, wetting the fungal-wood mixture with water.

Figure 8:
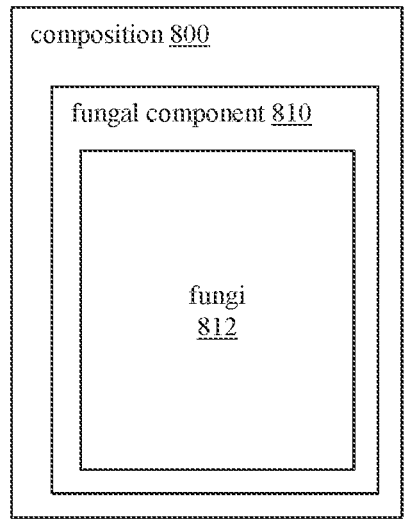
FIG. 8 is a block diagram illustrating a composition, according to some embodiments of the present disclosure.

FIG. 8 is a block diagram that describes a composition 800, according to some embodiments of the present disclosure. In some embodiments, the composition 800 may include a fungal component 810. The fungal component 810 may include fungi 812 that may be controllably cultured. In some embodiments, at least one fungus of the fungi 812 may be included in an immature fungal mixture. In some embodiments, the composition 800 may be a wood chip inoculum.

Figure 9:
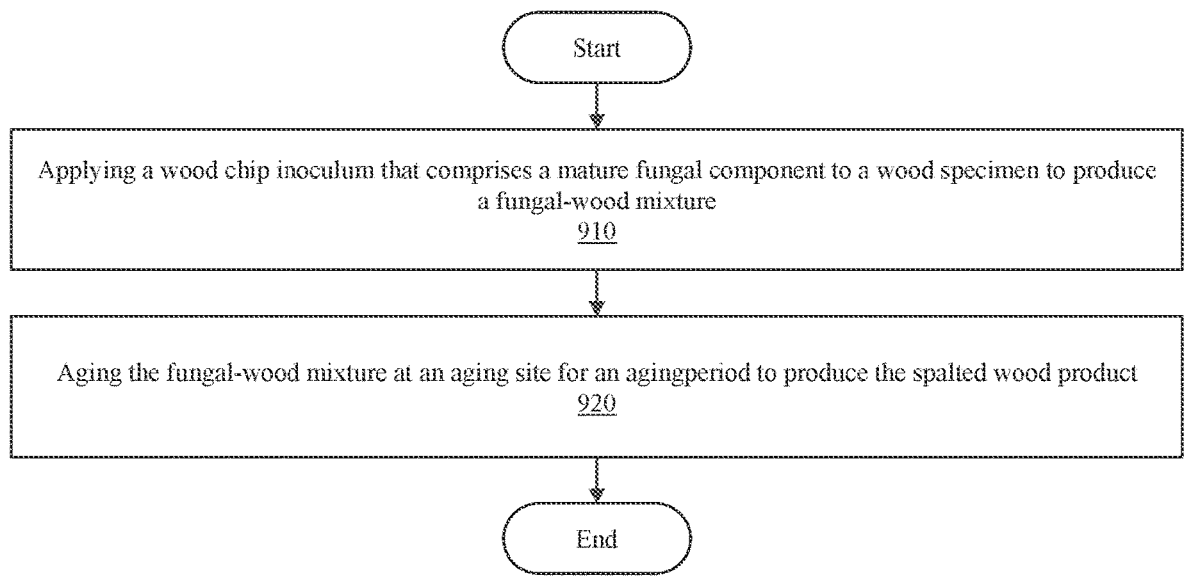
FIG. 9 is a flowchart illustrating a method, according to some embodiments of the present disclosure.

FIG. 9 is a flowchart that describes a method, according to some embodiments of the present disclosure. In some embodiments, at 910, the method may include applying a wood chip inoculum that comprises a mature fungal component to a wood specimen to produce a fungal-wood mixture. At 920, the method may include aging the fungal-wood mixture at an aging site for an aging period to produce the spalted wood product.

Figure 10:
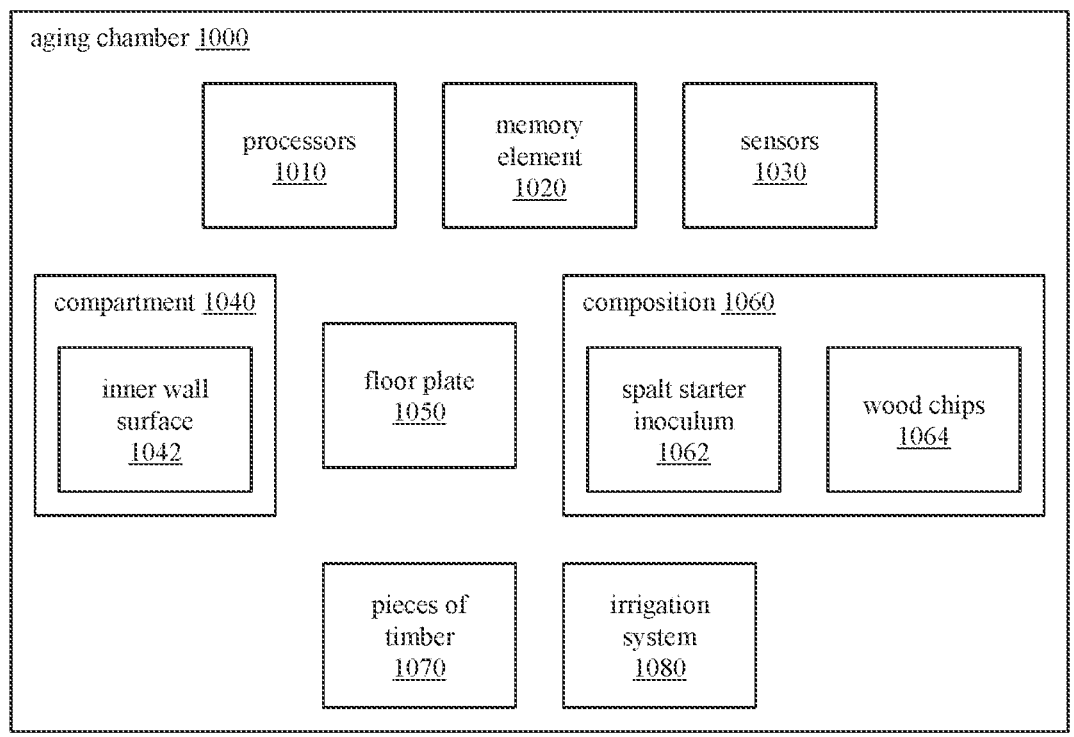
FIG. 10 is a block diagram illustrating an aging chamber, according to some embodiments of the present disclosure.

FIG. 10 is a block diagram that describes an aging chamber 1000, according to some embodiments of the present disclosure. In some embodiments, the aging chamber 1000 may include one or more processors 1010, a compartment 1040, a floor plate 1050 located within the chamber, a composition 1060 for production of a spalted wood product disposed on the floor plate 1050, and one or more pieces of timber 1070 retained within the chamber and disposed over the composition 1060. The aging chamber 1000 may also include at least one memory element 1020, the at least one memory element 1020 configured to store instructions for controlling the one or more processors 1010, the at least one memory element retains sensor data.

In some embodiments, the aging chamber 1000 may also include one or more sensors 1030, the processor transmits data from the one or more sensors 1030 to the at least one memory element 1020. The aging chamber 1000 may also include an irrigation system 1080 electrically connected to the one or more processors 1010, the irrigation system 1080 may be activated, based on sensor data from the one or more sensors 1030, to dispense a substance into the chamber. The compartment 1040 may include an inner wall surface 1042 forming a chamber configured to retain timber. The composition 1060 may include a spalt starter inoculum 1062 and wood chips 1064.

Figure 11:
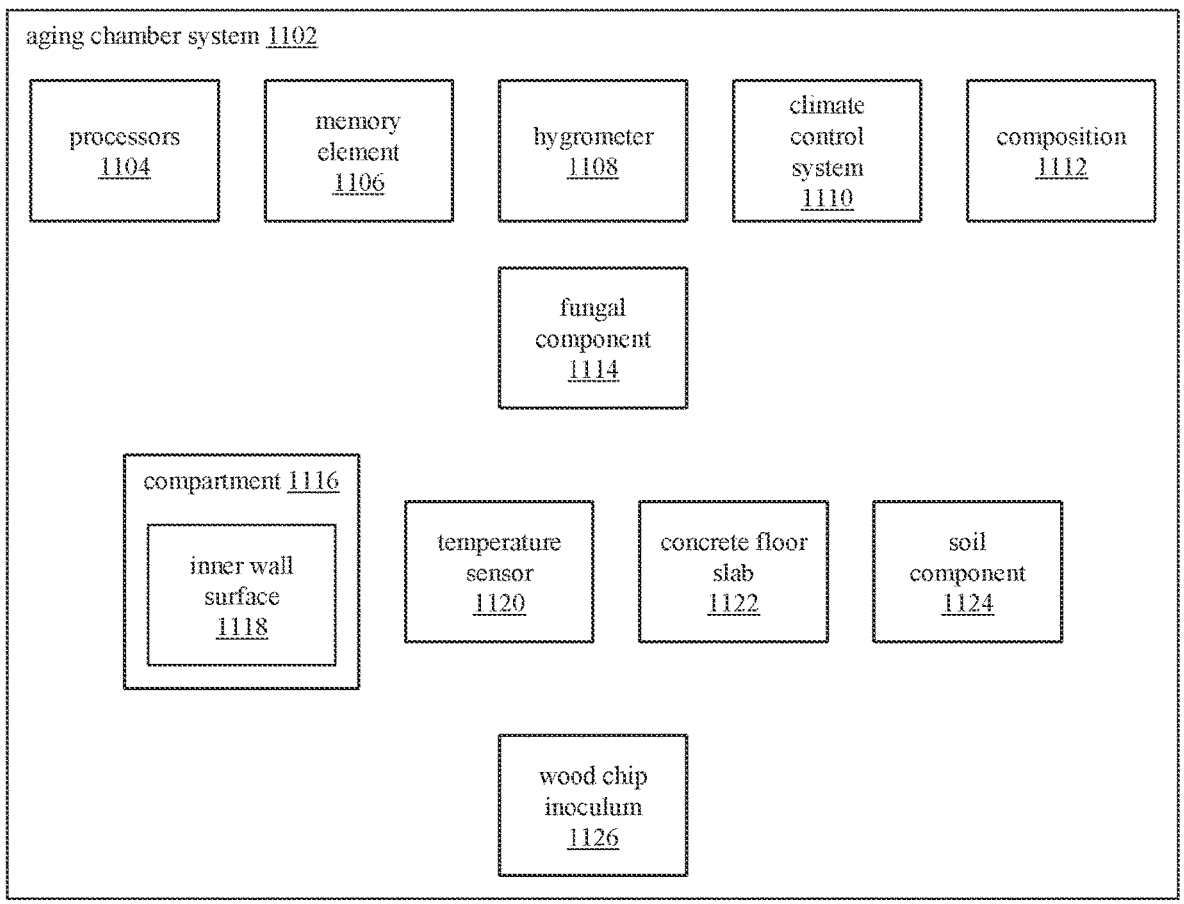
FIG. 11 is a block diagram illustrating an aging chamber system, according to some embodiments of the present disclosure.

FIG. 11 is a block diagram that describes an aging chamber system 1102, according to some embodiments of the present disclosure. In some embodiments, the aging chamber system 1102 may include one or more processors 1104, a compartment 1116, a climate control system 1110 to maintain a predetermined temperature, a concrete floor slab 1122, a composition 1112 for production of a spalted wood product disposed on the concrete floor slab 1122, a soil component 1124, a fungal component 1114, and a wood chip inoculum 1126. The aging chamber system 1102 may also include at least one memory element 1106, the at least one memory element 1106 configured to store instructions for controlling the one or more processors 1104, the at least one memory element retains sensor data.

In some embodiments, the aging chamber system 1102 may also include a hygrometer 1108. The hygrometer 1108 may be configured to measure humidity levels within the chamber. The processor transmits data from the hygrometer 1108 to the at least one memory element 1106. The aging chamber system 1102 may also include a temperature sensor 1120, the temperature sensor 1120 may be configured to measure the temperature of the chamber. The processor transmits data from the temperature sensor 1120 to the at least one memory element 1106. The compartment 1116 may include an inner wall surface 1118 forming a chamber configured to retain timber.

In some embodiments, the aging chamber system 1102 may also include a CO2 sensor, the CO2 sensor may be configured to measure the amount of CO2 within the chamber and maintain the level of CO2 within the chamber below approximately 400 ppm of CO2. The processor transmits data from the CO2 sensor to the at least one memory element 1106. In some embodiments, the aging chamber system 1102 may also include an oxygen (O2) sensor, the O2 sensor may be configured to measure the amount of oxygen within the chamber and maintain the level of CO2 within the chamber below approximately 400 ppm of CO2, the processor transmits data from the O2 sensor to the at least one memory element 1106.

In some embodiments, the aging chamber system 1102 may also include an irrigation system configured to regulate the moisture levels within the aging chamber, the irrigation system may be electrically connected to the processor. In some embodiments, the aging chamber system 1102 may include an overhead sliding track door. In some embodiments, the aging chamber system 1102 may include an opaque stretch liner disposed on one or more fungal-inoculated packets retaining the fungal component 1114.

In some embodiments, the aging chamber system 1102 may also include a layer of closed-cell polyurethane insulating material, the layer of closed-cell polyurethane material disposed on the inner wall surface 1118 of the chamber. In some embodiments, the concrete floor slab 1122 may include a heating system. In some embodiments, about 2 inches to about 10 inches of B-horizon soil disposed on the concrete floor slab 1122.

Figure 12:
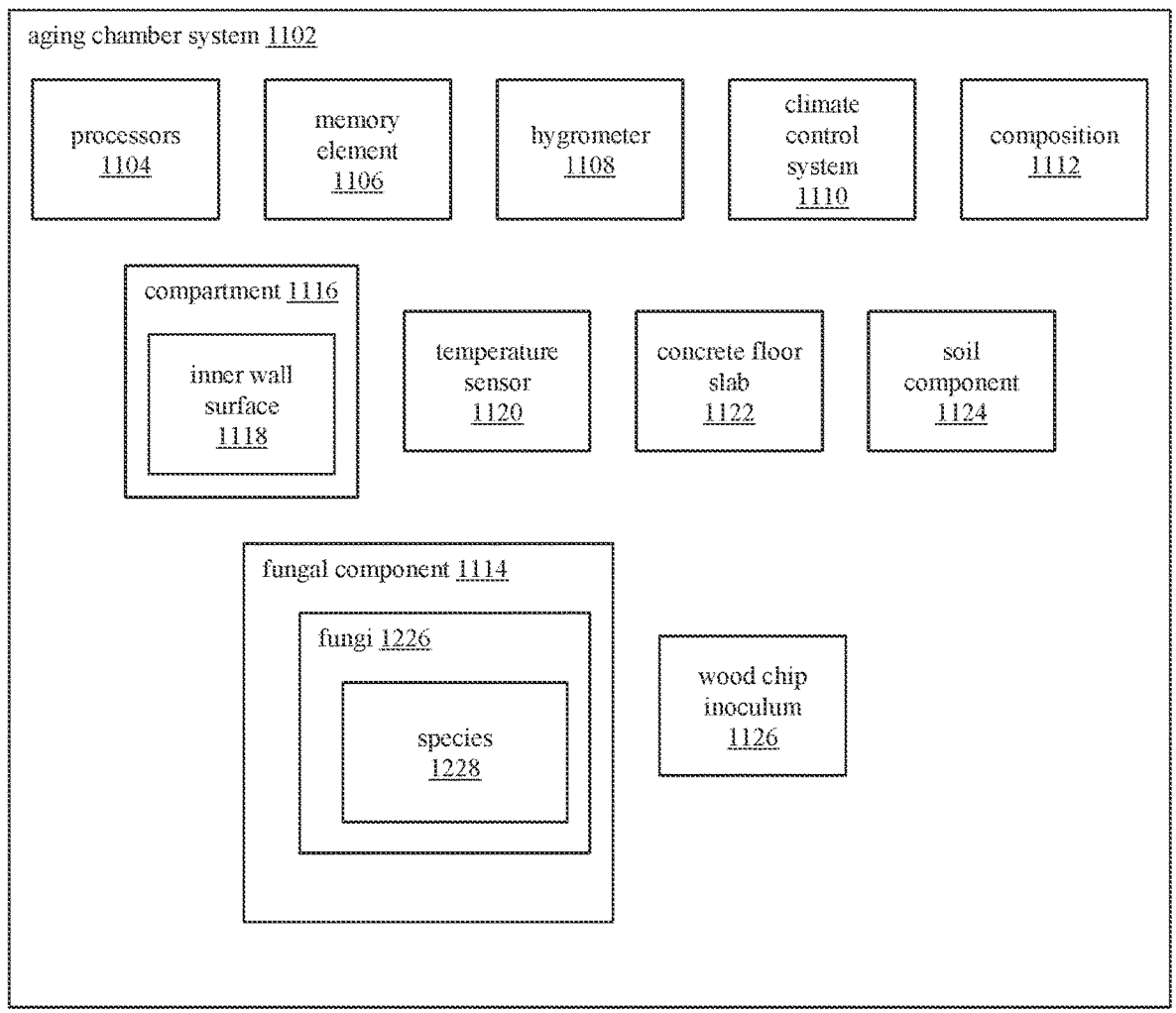
FIG. 12 is a block diagram further illustrating the aging chamber system from FIG. 11, according to some embodiments of the present disclosure.

FIG. 12 is a block diagram that further describes the aging chamber system 1102 from FIG. 11, according to some embodiments of the present disclosure. In some embodiments, the fungal component 1114 may include one or more fungi 1226 selected from a group. The one or more fungi 1226 may also include a species 1228 of any genus.

Figure 13:
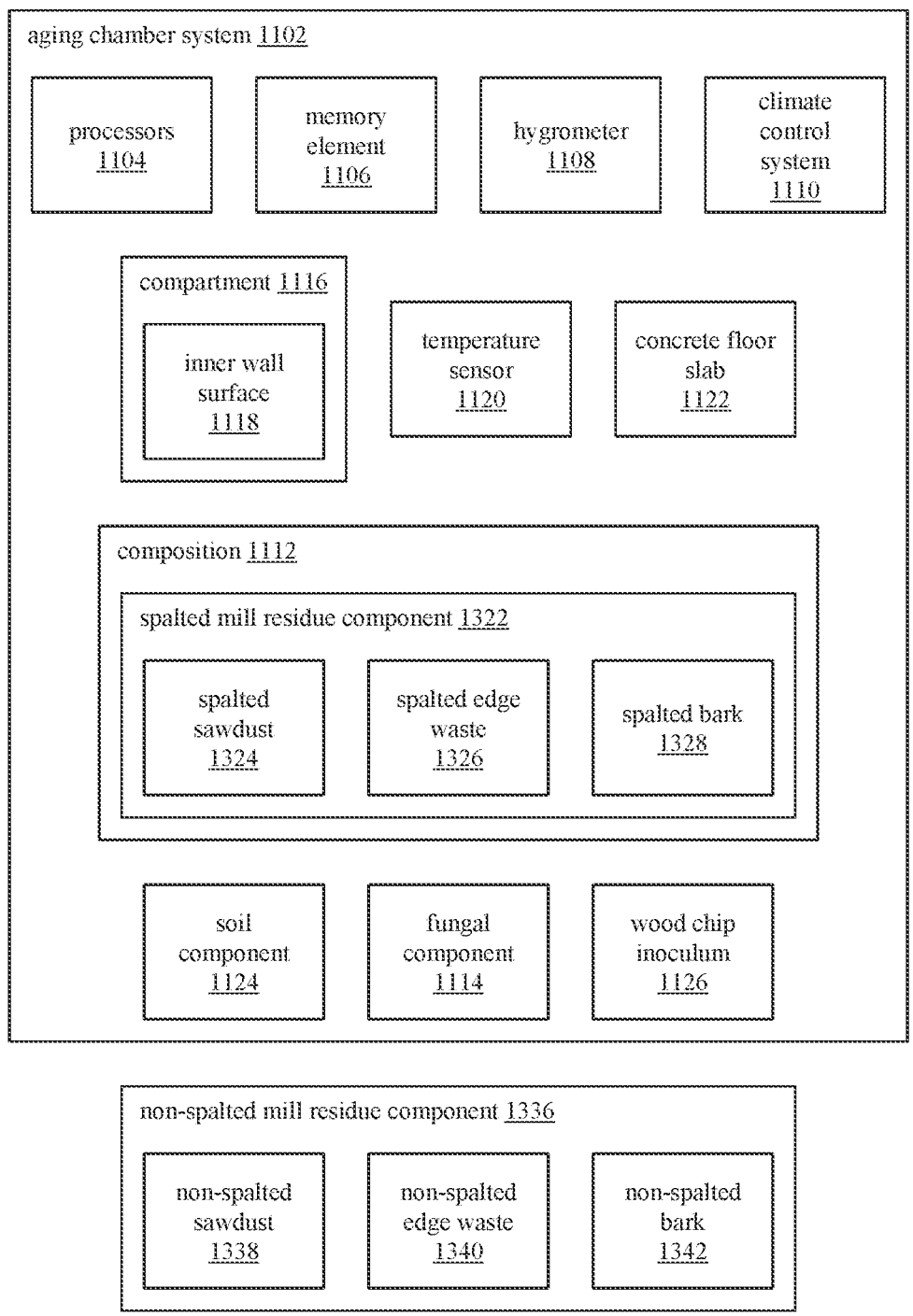
FIG. 13 is a block diagram further illustrating the aging chamber system from FIG. 11, according to some embodiments of the present disclosure.

FIG. 13 is a block diagram that further describes the aging chamber system 1102 from FIG. 11, according to some embodiments of the present disclosure. In some embodiments, the composition 1112 may include a spalted mill residue component 1322. The spalted mill residue component 1322 may include spalted sawdust 1324, spalted edge waste 1326, and spalted bark 1328. In some embodiments, the spalted mill residue component 1322 mixed with a non-spalted mill residue component 1336. The non-spalted mill residue component 1336 may include non-spalted sawdust 1338, non-spalted edge waste 1340, and non-spalted bark 1342.

Figure 14:
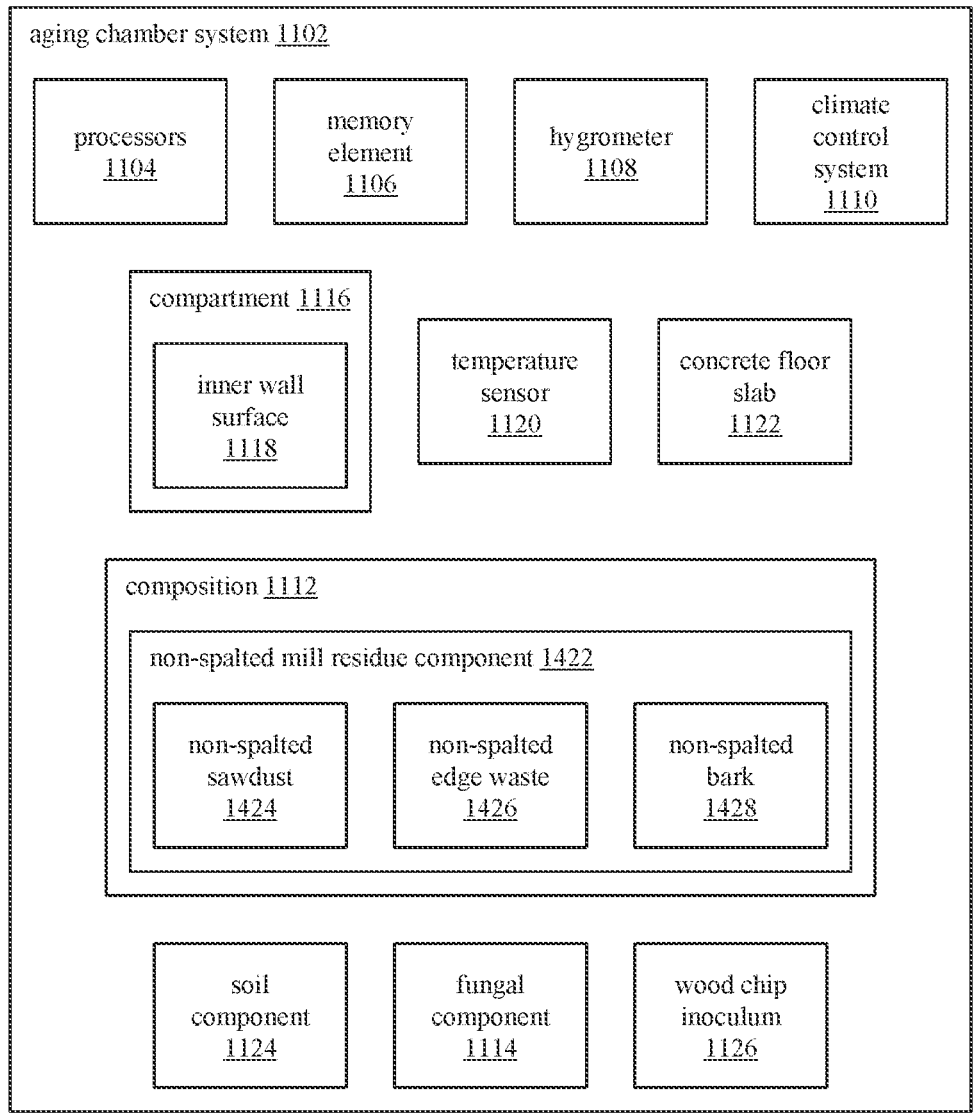
FIG. 14 is a block diagram further illustrating the aging chamber system from FIG. 11, according to some embodiments of the present disclosure.

FIG. 14 is a block diagram that further describes the aging chamber system 1102 from FIG. 11, according to some embodiments of the present disclosure. In some embodiments, the composition 1112 may include a non-spalted mill residue component 1422. The non-spalted mill residue component 1422 may include non-spalted sawdust 1424, non-spalted edge waste 1426, and non-spalted bark 1428.

Figure 15:
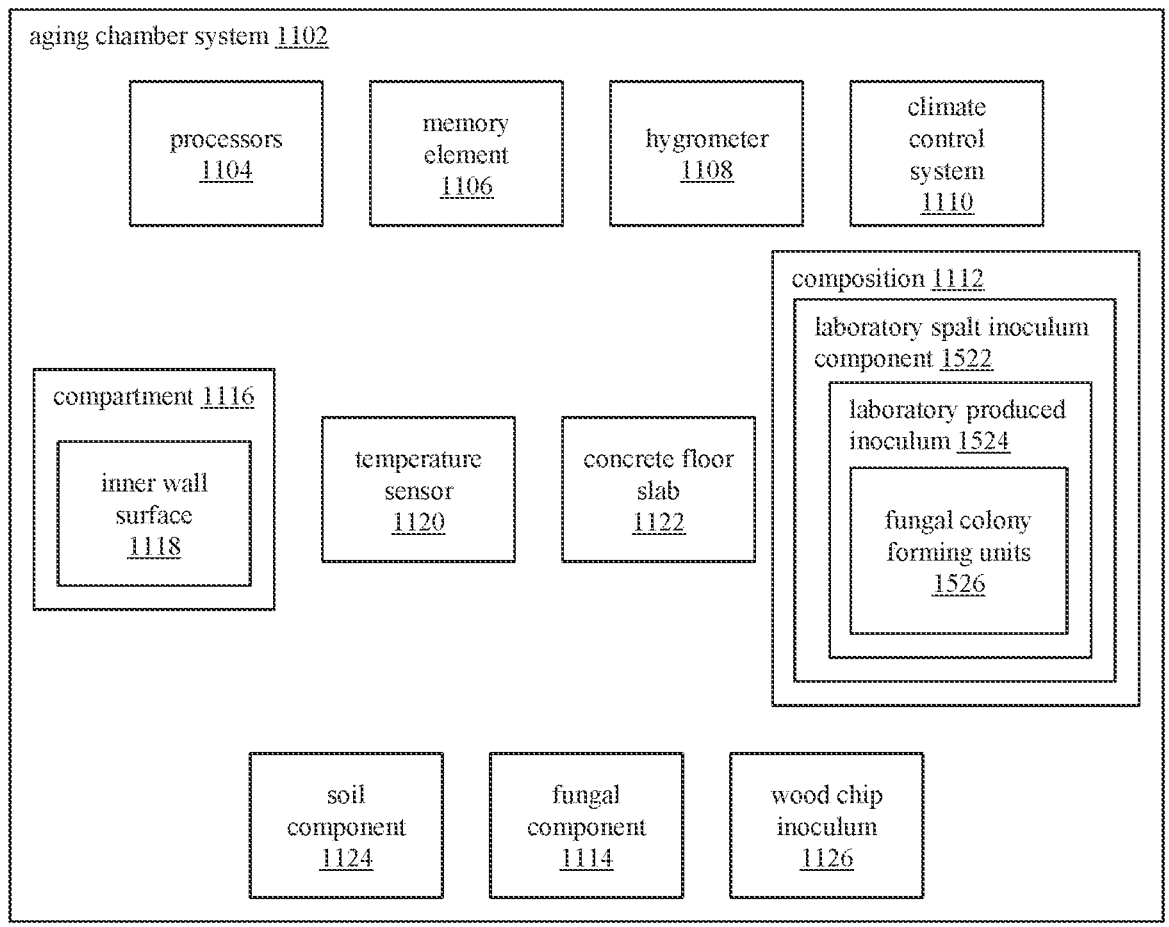
FIG. 15 is a block diagram further illustrating the aging chamber system from FIG. 11, according to some embodiments of the present disclosure.

FIG. 15 is a block diagram that further describes the aging chamber system 1102 from FIG. 11, according to some embodiments of the present disclosure. In some embodiments, the composition 1112 may include a laboratory spalt inoculum component 1522. The laboratory spalt inoculum component 1522 may include a laboratory produced inoculum 1524. The laboratory produced inoculum 1524 may also include one or more fungal colony forming units 1526 CFUs selected from one or more of rye berries, sterile non-spalted sawdust, and a sterile non-spalted wood chip mixture.

Figure 16B:
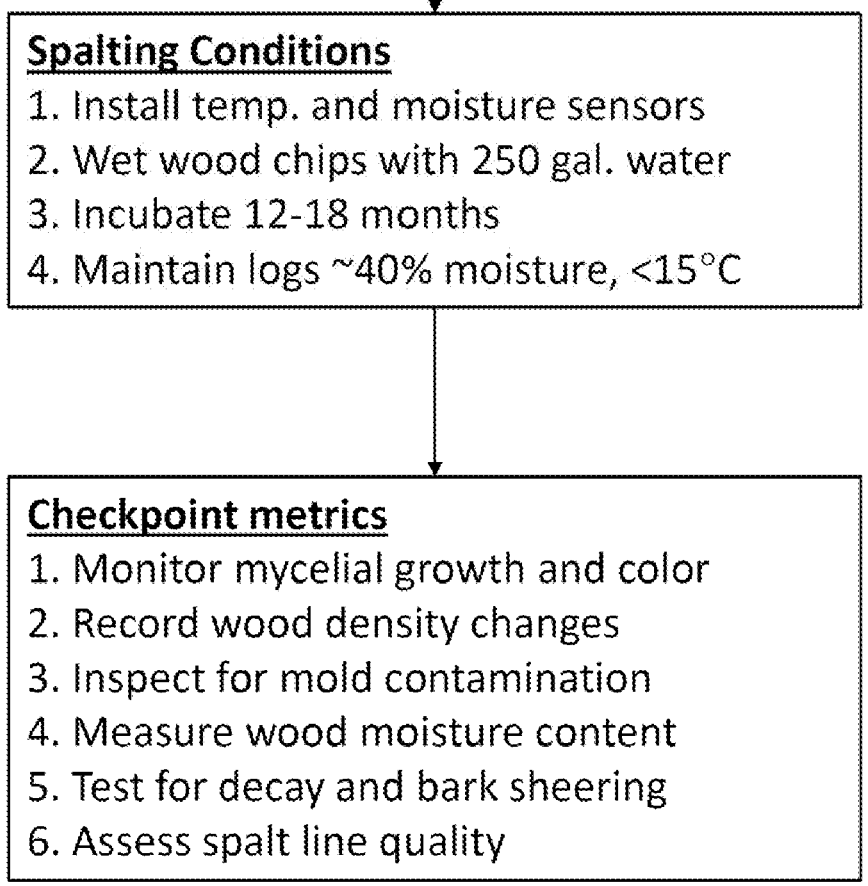

FIGS. 16A and 16B illustrate spalting conditions. Referring first to FIG. 16A, Wood Chip Inoculum may include the steps: Harvest 6 ft 3 forest topsoil, Mix in 1 ft 3 spalt inoculum A, Incubate 2-3 months at 5-15° C., Monitor fungal development, Add 2700 ft 3 mill residue, and combine using a front loader. Next, the Hardwood Substrate includes: Winter cut ~200 maple logs, Fungi colonize at forest site, Sporulation on log ends ~2 days, Select grade 2 veneer logs, and Transport logs to aging site. Next, Aging Site Preparation includes: Select a level site ~100×40 ft., Clear organic 'O' surface soil, Remove 'A' horizon soil ~1 ft. D, Lay 6" of wood chip inoculum, Stack 10 ft. cut logs 100 L×3 D×3 H, and Overlay with 6" inoculum. Finally, Checkpoint metrics may include: Monitor mycelial growth and color, Record wood density changes, Inspect for mold contamination, Measure wood moisture content, Test for decay and bark sheering, and Assess spalt line quality.

Definitions

It is to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this present disclosure belongs. In this specification and in the claims which follow, reference will be made to a number of terms which shall be defined herein.

As used in the specification and the appended claims, the singular forms "a," "an," and "the" include plural referents unless the context clearly dictates otherwise. Thus, for example, reference to "an opening" can include two or more openings.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally affixed to the surface" means that it can or cannot be fixed to a surface.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; and the number or type of aspects described in the specification.

Disclosed are the components to be used to manufacture the disclosed devices, systems, and articles of the present disclosure as well as the devices themselves to be used within the methods disclosed herein. These and other materials are disclosed herein, and it is understood that when combinations, subsets, interactions, groups, etc. of these materials are disclosed that while specific reference of each various individual and collective combinations and permutation of these materials cannot be explicitly disclosed, each is specifically contemplated and described herein. For example, if a particular material is disclosed and discussed and a number of modifications that can be made to the materials are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination material, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the articles and devices of the present disclosure. Thus, if there are a variety of additional steps that can be performed it is understood that each of these additional steps can be performed with any specific aspect or combination of aspects of the methods of the present disclosure.

It is understood that the devices and systems disclosed herein have certain functions. Disclosed herein are certain structural requirements for performing the disclosed functions, and it is understood that there are a variety of structures that can perform the same function that are related to the disclosed structures, and that these structures will typically achieve the same result.

Devices And Systems

In various aspects of the disclosure, an aging chamber is provided for use to age fungal-wood mixtures to produce spalted wood products. The aging chamber device may be particularly advantageous for indoor aging procedures. In one or more embodiments, the aging chamber may be placed in an outdoor environment for use. Accordingly, the aging chamber device may be used in any suitable setting without departing from the scope of the disclosure.

The aging chamber device may provide a separate moisture-controlled and temperature-controlled environment for inducing indoor spalt lines of multiple logs (e.g., about 40 logs) or cut lumber stacks. The device may be used at any time, but in particular, may be used when outdoor space and/or availability of wood chips is limited. The aging chamber device includes an overhead sliding track door (e.g., 22 feet wide×16 feet tall) and walls enclosing a dark interior (i.e., a light-limited environment) with one access door built onto a radiant heated concrete floor slab. The chamber may be insulated using closed-cell spray foam polyurethane foam and a 'log-cradle' may be buttressed with steel beams for safety. The chamber may be ventilated with industrial fans and chilled to about 12-15° C. using medium-temperature range chiller.

Regarding the soil, soil horizon may be defined as the parallel layer of the soil surface. Each layer has its own composition of physical, chemical and biological characteristics, they quite differ from each of the layers above and beneath each layer. Horizons have definite physical features such as the color and texture of each layer of the soil. The uppermost layer of the topsoil is composed of organic materials like dried leaves, grasses, and other decomposed organic matter. This layer of soil is blackish brown or dark brown in color, the color is for the content of organic material. The A-Horizon is also known as the Topsoil. This layer is also rich in organic material and commonly known as the humus layer. This majorly consists of both organic matter and other decomposed type materials. The topsoil is very soft and is thus porous in nature to hold enough air and water. The E-Horizon layer has nutrients seeped down from the O and A horizons. This layer is very common in forested areas which have low clay content. The B-Horizon or Subsoil is present just below the topsoil, while above the bedrock. This is comparatively much harder and more compact than the topsoil. This contains less humus, soluble minerals, and organic matter. Rather this is a site of deposition of certain minerals and metal salts like iron oxide. The C-Horizon, known as the Saprolite has an absence of any organic matter and is made up of broken bedrock. The R-Horizon is the compacted and cemented layer with different types of rocks like granite, basalt and limestone.

To use the aging chamber device in a method for producing a spalted wood product, about 6 inches of B-horizon soil and a specified combination of fungal isolates and wood chips may be added to the floor slab. Logs or industry standard packets of pre inoculated variable, pre-sawn lumber (e.g., about 4-10 inches wide×10 feet long×1.5 inches thick) may be arranged as flat stacks within the aging chamber (e.g., about 18 rows tall×48 inches wide with no space between lumber of irrigated, fungal-inoculated packets that have been wrapped with opaque stretch liner around the outer edges and sides but not on or below the widest faces of the stacks). In other words, the packets are wrapped around all four sides of the stacks, the top of the stacks, and not the bottom of the stacks. Spacers of about 4 inches of wood may separate each wrapped-packet on the unwrapped, open-faces, and may provide airflow and a sampling window. Up to sixteen packets of wrapped pre-cut hardwood lumber may be stacked in this manner and vented for CO2 byproduct of fungal decay such that the interior of the device remains below 400 ppm CO2 using a fan and medium temperature range chiller (e.g., an 18 BTU AC unit). In one or more embodiments various other air conditioning units and fan combinations may be used.

Devices and systems may be used for monitoring, sampling, analyzing, and/or adjusting spalting conditions to ensure that spalting progresses according to a planned or suitable timeline and/or according to a desired quality or characteristic of the resultant spalted wood product. For example, in certain embodiments, controlled moisture and temperature are key factors for effective production of spalted wood products, so devices and systems for monitoring moisture content or humidity and temperature are needed to ensure that the process proceeds according to plan.

Accordingly, a humidity sensor (i.e., a device that senses, measures, and reports the humidity or relative humidity of a gas) may be used to provide a measurement of water vapor present within air that is at or within an aging site. The humidity sensor may be operationally coupled with a monitor system, such as a computer system, configured to receive, store, and analyze sensor inputs. Another type of sensor that may be used is a thermometer, which can be used to measure a temperature at or within the aging site and may be operably coupled with the monitor system or computer system. Other elements may be included, such as climate control elements that may be automated or semi-automated to facilitate management of the process. These may include a sprinkler system, a heating element, a cooling element, a ventilation element, and the like. Other sensors that may be used include a CO2 sensor and/or an O2 sensor.

In embodiments, logging or wood operation hardware may be used, such as shovels and spades, axes and saws, transportation equipment and machinery such as lifts and trucks, storage means, and lumber processing equipment and machinery. In embodiments wherein methods for culturing and/or propagating fungi species are implemented, biotechnological devices and systems may be used, including but not limited to a biosafety hood, laboratory equipment such as biochemicals and glassware, fungi culture compositions and necessary equipment, and laboratory instrumentation, as is generally known in the art.

Compositions and Methods

In various aspects, the disclosure provides methods for production of spalted wood products and compositions that may be utilized in the methods. A composition for production of a spalted wood product may be comprised of a fungal component that comprises fungi that have been controllably cultured such that the cultured fungi have markedly different characteristics compared to any naturally occurring counterpart. The cultured fungi, which may have been selectively cultured under controlled conditions for propagation prior to use, generally may be used to effectively produce spalted wood products on a commercial scale. By identifying fungi that facilitate wood spalting when present in an inoculation at certain ratios those compositions can be utilized in the corresponding methods of production.

In embodiments, the composition may be a wood chip inoculum which may include various combinations of various components. Components may include: one or more of a soil component comprising topsoil, A horizon soil, B horizon soil, or a mixture or combination of A horizon and B horizon soil; a spalted mill residue component comprising spalted sawdust, spalted edge waste, and spalted bark; a non-spalted mill residue component comprising non-spalted sawdust, non-spalted edge waste, and non-spalted bark; a mill residue mixture component comprising the spalted mill residue component mixed with the non-spalted mill residue component; a laboratory spalt inoculum component comprising a laboratory produced inoculum further comprising one or more fungal CFUs from one or more of rye berries, sterile non-spalted sawdust, and a sterile non-spalted wood chip mixture; a mature spalt inoculum component comprising aged spalt inoculum.

In at least one embodiment, the initial composition may be a horizon soil component, a non-spalted mill residue component, and a laboratory spalt inoculum component. In one or more embodiments, the composition may include a non-spalted mill residue component, a spalted mill residue component, and a mature spalt inoculum component. In one or more embodiments, the composition may include a non-spalted mill residue component, a spalted mill residue component, and a laboratory spalt inoculum component. In one or more embodiments, the composition may include a non-spalted mill residue component, a spalted mill residue component, a mature spalt inoculum, and a horizon soil component.

In one or more further embodiments, an initial composition may comprise a horizon soil component, a non-spalted mill residue component, and a laboratory spalt inoculum component. In one or more further embodiments, an ongoing composition may comprise a mill residue mixture component and a mature spalt inoculum component. In one or more further embodiments, an ongoing composition may comprise a mill residue mixture component, a mature spalt inoculum component, and a laboratory spalt inoculum component. In one or more further embodiments, an ongoing composition may comprise a horizon soil component, a mill residue mixture component, a mature spalt inoculum component, and a laboratory spalt inoculum component.

In the one or more aforementioned embodiments, they may further comprise combinations as described herein within an acceptable range of values and tolerances conventionally understood when preparing wood products in the lumber industry. For example, in at least one embodiment, a mature spalt inoculum component and a mill residue component that is comprised of an approximately 3:1 ratio of debarked healthy, unspalted maple chips to spalted sawdust and/or spalted edge waste and/or spalted bark.

In general, a method for producing a spalted wood product comprises applying a wood chip inoculum that comprises a mature fungal component to a wood specimen to produce a fungal-wood mixture and aging the fungal-wood mixture at an aging site for an aging period to produce the spalted wood product. The wood specimen may comprise a basswood specimen, a beech specimen, a poplar specimen, a sugar maple specimen, and/or a yellow birch specimen. The aging period may vary depending on the species of the specimen and/or other aging conditions. In embodiments, the wood chip inoculum further comprises a soil component and a mill residue component that is comprised of an approximately 3:1 ratio of debarked healthy spalted maple chips to spalted sawdust and/or spalted edge waste and/or spalted bark.

In various embodiments, the wood chip inoculum may be produced by inoculating debarked healthy maple chips with a mature spalt inoculum component with an immature fungal component that comprises a plurality of fungi to produce a mature spalt inoculum-fungal mixture, incubating the mature spalt inoculum-fungi mixture, and monitoring fungal development, for about 2-3 months, at about 5-15° C. to produce the mature fungal component, and combining a mill residue component with the mature fungal component to produce the wood chip inoculum.

In embodiments, the aging site is prepared by selecting a level site, clearing organic 'O' surface soil from the level site, removing 'A' horizon soil to a depth of about 1 foot from the level site, laying about 6 inches of the wood chip inoculum to the level site, stacking about 10 feet of the wood specimen over the wood chip inoculum, and overlaying the wood specimen with about 6 inches of wood chip inoculum. In one or more embodiments, the logs may be ten feet long and laid into the aging site end-to-end. As such, three ten-foot-long logs end-to-end sit thirty feet long. The logs are on average sixteen inches in diameter making a stack of logs approximately forty-eight inches in height by thirty feet wide and one hundred feet long.

In embodiments, the wood specimen may be harvested by winter cutting a plurality of logs from a forest, allowing a plurality of forest fungi to colonize on the plurality of logs while in the forest, and transporting the plurality of logs from the forest to the aging site.

In embodiments, the method includes monitoring spalt conditions of the fungal-wood mixture during the aging period and adjusting the conditions if necessary to produce the spalted wood product within the aging period.

In embodiments, the spalt conditions may include about 40% moisture and a temperature that is less than about 15° C. Monitoring spalt conditions may comprise monitoring mycelial growth and color, recording any changes in density of the wood specimen, inspecting the fungal-wood mixture for mold contamination, measuring moisture content of the fungal-wood mixture, testing the fungal-wood mixture for decay and bark sheering, and assessing quality or effectiveness of the method for producing the spalted wood product. In embodiments, adjusting spalt conditions comprises wetting the fungal-wood mixture with water. In one or more embodiments, adjusting spalt conditions may include additional adjustments such as using heat, steam, or other means to adjust conditions.

In various aspects, the ratios and concentrations of fungal CFU's with rye berries, sawdust, and wood chip mix are effective to transform any fungi into highly productive fungi capable of spalting wood at an unnatural rate. In other aspects, the aging site preparation steps that involve a wood chip cover-mix in specific ratios transforms the aging site into a highly productive aging site capable of spalting wood at an unnatural rate. Further, in other aspects, the methods for monitoring decay or spalting, and spalt sampling, may require an individual with mycological knowledge, technical skills, and familiarity of density measurement tools and volatiles to recognize the termination point for spalting.

In at least some embodiments, each step of a method may be required to be performed in a specific sequence and under controlled environmental conditions to produce spalting patterns on hardwood logs or milled lumber. Recognition of decay progression and knowledge of fungal development with wood density changes may be crucial for determining the endpoint of the process and to maintain wood structural integrity.

In one or more embodiments, different spalting fungi mixes may be used to stain the wood blue or red instead of creating zone lines. The process has been reproducible for maple, ash, and beech logs or lumber, and may be reproducible for other hardwood or softwood with fungal combinations to induce spalting. The size of outdoor or indoor environments and amounts of logs or lumber may be scaled up or down to achieve different types and/or amounts of spalting. In embodiments, irrigation and/or watering, spalting and/or zone lines, use of polyurethane and/or plastic wrap, use of inoculum and/or Fungal mix are effective to produce a desired result. Table 1 illustrates a listing of a plurality of fungi known to spalt, decolorize, and/or stain wood. In various embodiments, one or more fungus of a species of genus, of the listing of fungi of Table 1, may be included in the composition. The assessment of fungal pigmentation through agar plate testing and on wood specimens involves the examination and analysis of coloration patterns exhibited by fungi. This process encompasses detailed investigations into the chromatic characteristics manifested during fungal growth on agar plates, as well as the study of pigmentation patterns observable on wood substrates. In various embodiments, at least one fungus of the fungi in the composition is a species of genus one or more of the following: *Penicillium variabile*, Sopp, *Fusarium culmorum* (W. G. Sm.) Sacc., *Coryne microspore*, Ellis & Everh., *Diatrypella placenta*, Rehm, *Arthrographis cuboidea* (Sacc. et Ellis) Sigler, *Poria aurea*, Peck, *Corticium polosum*, Burt, *Trametes* spp., *Xylaria* spp., *Trichaptum*, *Pholiota*, *Bjerkandera*, *Kretzschmaria* spp., *Daldinia*, *Armillaria* spp., *Lentinus cyathiformis* Bres., *Lecythophora hoffinannii* (van Beyma) W. Gams & McGinnis, *Tyromyces balsameus*, (Peck) Murrill, *Trogia crispa* Fr., *Polyporus dryophilus*, Berk., *Polyporus dryophilus* var., *vulpinus* (Fr.) Overh., *Peniophora piceae* (Pers.) J. Erikss., *Sporotrichum dimorphosporum*, v. Arx., *Gliocladium verticilloides*, Pidoplichko, *Nectria ochroleuca* (Schweinitz) Berkeley, *Trichoderma alroviride* P. Karst., *Trichoderma* sp., *Verticillium* sp., *Chlorosplenium aeruginascens* (Nyl.) Karst, *Scytalidium lignicola*, Pesante, *Ophiostoma piceae* (Münch), Syd., H. & P. Syd., *Aureobasidium pullulans* (deBary) Arnaud, *Phialophora alba* von Beyma, *Penicillium expansum*, *Penicillium implicatum*, Biourge, *Fusarium verticillioides*, (Sacc.) Nirenberg, *Dactylium dendroides* (Bulhard) Fr., *Phialemonium dimorphosporum*, W. Gams & W. B. Cooke, *Fusarium oxysporum*, Schlechtend.: Fr., *Ascocoryne cylichnium* (Tul.) Korf, and *Cephalotheca purpurea* (Shear) Chesters.

TABLE 1

Coloration Patterns of Fungi in Agar Plate Testing and on Wood Specimens

| Number | Fungal code | Fungal species | Color on agar | Color on wood |
|---|---|---|---|---|
| 1 | FTK 659B | *Penicillium variabile* Sopp | Red | No coloring |
| 2 | FTK 750A | *Fusarium culmorum* (W. G. Sm.) Sacc. | Red | Purple |
| 3 | FTK 239A | *Coryne microspora* Ellis & Everh. | Light brown | No coloring |
| 4 | FTK 430A | *Diatrypella placenta* Rehm | Light brown | No coloring |

TABLE 1-continued

Coloration Patterns of Fungi in Agar Plate Testing and on Wood Specimens

| Number | Fungal code | Fungal species | Color on agar | Color on wood |
|---|---|---|---|---|
| 5 | FTK 706B | *Arthrographis cuboidea* (Sacc. et Ellis) Sigler | Light brown | Red |
| 6 | FTK 110A | *Poria aurea* Peck | Brown | Red |
| 7 | FTK 534A | *Corticium polosum* Burt | Brown | Brown |
| 8 | FTK 795A | *Lentinus cyathiformis* Bres. | Brown | Brown |
| 9 | FTK 893A | *Lecythophora hoffmannii* (van Beyma) W. Gams & McGinnis | Brown | Brown |
| 10 | FTK 79A | *Tyromyces balsameus* (Peck) Murrill | Dark brown | Brown |
| 11 | FTK 473C | *Trogia crispa* Fr. | Dark brown | Brown |
| 12 | FTK 482B | *Polyporus dryophilus* Berk. | Dark brown | Brown |
| 13 | FTK 483A | *Polyporus dryophilus* var. *vulpinus* (Fr.) Overh. | Dark brown | Brown |
| 14 | FTK 840A | *Peniophora piceae* (Pers.) J. Erikss. | Dark brown | Brown |
| 15 | FTK 306D | *Sporotrichum dimorphosporum* v. Arx. | Yellow | No coloring |
| 16 | FTK 790A | *Gliocladium verticilloides* Pidoplichko | Yellow | Grayish yellow |
| 17 | FTK 843C | *Nectria ochroleuca* (Schweinitz) Berkeley | Yellow | Grayish yellow |
| 18 | FTK 585E | *Trichoderma atroviride* P. Karst. | Yellowish orange | Grayish brown |
| 19 | FTK 872B | *Trichoderma* sp. | Yellowish orange | Yellowish brown |
| 20 | FTK 164C | *Verticillium* sp. | Green | Green |
| 21 | FTK 401A | *Chlorosplenium aeruginascens* (Nyl.) Karst | Green | Green |
| 22 | FTK 197P | *Scytalidium lignicola* Pesante | Dark blue | Grayish blue |
| 23 | FTK 387AN | *Ophiostoma picede* (Münch) Syd., H. & P. Syd. | Dark blue | Grayish brown |
| 24 | FTK 132I | *Aureobasidium pullulans* (deBary) Arnaud | Black | Black |
| 25 | FTK 772A | *Phialophora alba* von Beyma | Pink | Light Brown |
| 26 | FTK 828A | *Penicillium expansum* Link | Pink | Gray |
| 27 | FTK 837A | *Penicillium implicatum* Biourge | Pink | Green |
| 28 | FTK 754A | *Fusarium verticillioides* (Sacc.) Nirenberg | Light purple | Light Brown |
| 29 | FTK 597A | *Dactylium dendroides* (Bulliard) Fr. | Purple | Purple |
| 30 | FTK 669A | *Phialemonium dimorphosporum* W. Gams & W. B. Cooke | Purple | Purple |
| 31 | FTK 31A | *Fusarium oxysporum* Schlechtend.: Fr. | Dark purple | Brown |
| 32 | FTK 392A | *Ascocoryne cylichnium* (Tul.) Korf | Dark purple | Brownish purple |
| 33 | FTK 433A | *Cephalotheca purpurea* (Shear) Chesters | Dark purple | Light Brown |

In embodiments, the invention may work better with installation and use of HEPA filters at fans or entrances to minimize cross contamination by unwanted organisms, observation "stations," or cameras internal to the chip pile or lumber stacks used to monitor inaccessible portions, or automated sprinkler irrigation with drops in moisture detection or vent opening with upper $CO_2$ limit detection.

In embodiments, the invention may not work if the internal wood pile or lumber stack temperatures rise above about 18° C. which can promote growth of secondary molds which can outcompete the spalting fungal mix. The invention also may not work if logs or lumber are allowed to dry out below about 30% moisture. The preferred wood chip source may be maple for maintaining populations of spalting fungi, and in embodiments, the diameter and length of logs may be about 2-3 ft.×10 ft. The maple wood chips, the fungal mix of 3-4 isolates and species, and the hardwood logs or pre-sewn lumber may be utilized in suitable ratios to achieve the desired result.

In embodiments, the spalted wood logs derived from a semi-controlled outdoor method, in particular, may be less friable than wild-crafted, forest derived spalted logs that are variable of their state and progress of decay, thereby providing improved mechanical strength to facilitate cuts for veneer production or other downstream uses such as wood turning. The disclosed methods for inducing spalt lines overcomes the time and rarity limitations of natural-sought, forest produced spalted wood as these methods reliably spalt 200 logs within 12-18 months per chip pile, and wood decay is halted prior to structural deterioration with the use wood density monitoring, fungal developmental progression, and biweekly destructive sampling. In embodiments, the spalt line patterns may generally be unique and unpredictable in both nature and the controlled environment, i.e., such that the final product has spalt lines that are unique or unpredictable to give a desired aesthetic appearance.

The disclosure provides commercial scale methods and conditions for establishing controlled, outdoor, and indoor, incubation environments to reliably induce decorative spalt line patterns of hardwood species using a specified combination of fungal isolates, hardwood chips, supplemental irrigation, and select lumber. This invention reduces the timeframe of producing spalted timber to about 12-18 months as compared to 3-20 years in nature. Lastly, the structural integrity of the spalted wood product is superior to and uniform compared to wild-crafted wood spalt, due to the domination of one fungal species versus multiple competing fungi (primary decomposers) that are consuming the wood fiber at various rates. Accordingly, the invention overcomes the time and scarcity limitations of natural-sought, forest-produced spalted wood by providing a steady, reliable source of product within a comparatively short timeframe.

Methods may utilize a fungal starter mix preparation, fungal bulking onto wood chips, outdoor aging site preparation, and installation of temperature-moisture-CO2 sensors, selection of hardwood logs and stacking one or more of the composition embodiments in addition to wood chip-mill residue, cover mix, irrigation, decay monitoring, sampling and measurements, termination of fungal decay, and milling. In embodiments, methods may include preparation of an indoor chiller room with temperature cycling controls and installation of temperature-moisture-CO2 sensors, selection and milling of hardwood logs, fungal wood chip mix preparation, irrigation of milled lumber, inoculation of milled lumber, polyurethane wrap, decay monitoring, sampling and measurements, termination of fungal decay, and veneer production.

The present disclosure provides a standardized outdoor method for inducing decorative spalt line patterns on hardwood logs using a specified combination of fungal isolates, wood chips, supplemental irrigation and select lumber which may be referred to as "chip piles" or "fungal-wood mixtures". The spalt starter inoculum is the first integral component of the invention and functions to induce pseudosclerotial plates, zone-line formation, and bleaching of hardwood logs as fungal development and wood decay progress through the wood. The spalt starter inoculum may be comprised of about 1 kg each of sterilized, water imbibed rye berries inoculated with $3\times10^7$ CFU/g of 3 cultured or propagated fungi. The preparation may be fully colonized in about 3 months at 15° C. into 1 cubic foot of fresh/new maple wood chips, 6 cubic feet of mature spalt inoculum and/or inoculated woodchips mature spalt inoculum, and 2700 cubic feet of mill residue mixed well using a front loader. The mill residue mix may be comprised of a 3:1 ratio of debarked fresh/new/unspalted healthy maple chips to spalted wood sawdust, spalted edge waste, and spalted bark.

In another embodiment, the system includes Spalt Starter Inoculum; Fungal Bulking onto Wood Chips; Outdoor Aging Site Preparation and Installation of Temperature-Moisture-CO2 sensors; Selection of Hardwood Logs and Stacking; Wood Chip-Mill Residue-Soil Cover Mix; Irrigation; Decay Monitoring, Sampling and Measurements; Termination of Fungal Decay and Milling; Preparation of Indoor Chiller Room with Temperature Cycling Controls and Installation of Temperature-Moisture-CO2 sensors; Selection and Milling of Hardwood Logs; Fungal Wood Chip Mix Preparation; Irrigation of Milled Lumber; Inoculation of milled lumber; and Polyurethane Wrap.

In an embodiment, spalting timelines for various species of wood including but not limited to: basswood, beech, poplar, sugar maple, and yellow birch. The timeline may vary or differ from what is shown for a particular species. For example, each species may have its own timeline to completion, for example, beech may be inoculated and/or colonized and aged to the point where it is losing density and is ready to be sawn at approximately 3-6 months faster than sugar maple.

In an embodiment, wood is identified by peeling back bark on the log surface to determine what level of aging has taken place.

Spalted Wood Products

In an embodiment, a spalted wood product may be produced by a method as disclosed herein, e.g., a method that comprises applying a wood chip inoculum that comprises a mature fungal component to a wood specimen to produce a fungal-wood mixture and aging the fungal-wood mixture at an aging site for an aging period to produce the spalted wood product. A spalted wood product may be processed into veneer or processed to produce a different spalted wood product, according to need.

In an embodiment, timber refers to wood that has been processed for various purposes, including construction, woodworking, and other applications. It includes both raw logs and processed lumber.

In an embodiment, the aging chamber system may have a moisture sensor, such as a humidity sensor or hygrometer. A hygrometer is a device designed to measure the moisture content or humidity levels in the air or in a material.

In an embodiment, the aging chamber system may have a sensor that measures temperature such as a thermometer or a temperature sensor. There are various types of temperature sensors, including thermocouples, thermistors, infrared thermometers, and resistance temperature detectors (RTDs), each using different principles to measure temperature.

In an embodiment, the aging chamber system may have a sensor that measures carbon dioxide (CO2) levels such as a carbon dioxide sensor or CO2 sensor. These sensors detect and quantify the concentration of CO2 gas in the surrounding environment. They may be used in the aging chamber system to monitor air quality to ensuring safe and healthy environments, particularly in enclosed spaces where high levels of CO2 may be detrimental to human health.

In an embodiment, the aging chamber system may have a refrigeration system that is designed to maintain specific temperatures within an enclosed space such as a "climate control system" or a "refrigeration system." It may also be referred to as a "cooling system" in some contexts. The system is designed to provide fresh air and remove stale air from the chamber or enclosed space and may be referred to as a "ventilation system." It helps to maintain air quality and circulation within the chamber or confined area. Ventilation systems may ensure a healthy and comfortable indoor environment of the aging chamber by regulating airflow, controlling humidity levels, and removing pollutants.

In an embodiment, the aging chamber system may have a radiant heated concrete floor slab being a type of heating system that is installed within a concrete floor to provide warmth to a room or space. It is also known as radiant floor heating. The heating system may have an embedded heating element: In this system, a heating element (usually a series of electric wires or pipes containing hot water) is embedded within the concrete floor slab during construction. Heat Transfer: When the system is activated, the heating element warms up. This, in turn, transfers heat directly to the concrete slab. Radiant Heat Emission: The heated concrete slab radiates heat upward, warming the room or space above it. This is a form of radiant heating, where warmth is emitted from a warm surface to heat the surrounding environment. Even Heat Distribution: Radiant floor heating provides a more even distribution of heat compared to traditional forced-air systems, where warm air rises from vents. With radiant heating, the entire floor becomes a heat source, creating a comfortable environment.

In an embodiment, the aging chamber system may have an irrigation or a sprinkler system for "moistening" or "sprinkling" a substance such as water droplets. This system is designed to regulate the moisture levels within the aging chamber to facilitate the proper curing and drying of the timber. It ensures that the timber remains at the desired moisture content, which is crucial for achieving the desired quality and characteristics in the wood.

In an embodiment, the aging chamber system may have an O2 sensor, or oxygen sensor to monitor and control the oxygen levels within the chamber. Maintaining specific levels of oxygen is crucial in the aging process of timber. Oxygen levels can influence factors like the rate of wood decay, microbial activity, and the overall quality of the aging process. Too much oxygen can lead to excessive decay and undesirable changes in the wood's properties. Conversely, too little oxygen may hinder the aging process. The O2 sensor provides real-time feedback to the control system of the aging chamber, allowing it to adjust the oxygen levels as needed to ensure optimal aging conditions. This helps to achieve consistent and high-quality results in the timber aging process.

Primary Outdoor Aging Grove/Piles

The present invention provides a standardized outdoor method for inducing decorative spalt line patterns within hardwood logs using a specified combination of fungal isolates, wood chips, supplemental irrigation or 'the chip piles'.

In an embodiment, the spalt starter inoculum functions to induce pseudosclerotial plates, zone-line formation and bleaching of hardwood logs as fungal development and wood decay progress through the wood.

In another aspect, the spalt starter inoculum may include 1 kg each of sterilized, water-imbibed rye berries inoculated with 3×107 CFU/g of 3 wild propagated fungi fully colonized in 3 months at 15° C. into 1 cubic foot of maple wood chips, 6 cubic feet of topsoil, and 2700 cubic feet of mill residue mixed well using a front loader. The mill residue mix is comprised of a 3:1 ratio of debarked healthy maple chips to spalted wood sawdust, edge waste and bark.

The second integral part of the system and method includes preparation of an outdoor aging site called a chip pile that serves as the medium for immobilizing and nourishing the fungal isolates and creating the spalting patterns of hardwood logs. The selected site is level, 100×40 feet in scale, and is cleared of organic 'O' surface soil and 1 ft. depth of 'A' horizon soil. The cleared site is overlaid with 6 inches of spalt starter inoculum onto which 200, 10 ft. cut hardwood logs are stacked 50 Long by 3 ft. wide by 3 ft. high. Three inspection passages of 2 ft×2 ft×5 ft are created along the center of the pile to allow space for a human to inspect spalt line progression. The passages are sealed off with a heavy metal sheet when not in use. A WeatherLink EnviroMonitor Wireless Station (DAVIS Instruments) is installed at the center of the pile remote sensors on a beam attached to 3 Temperature and 3 Soil Moisture SensorSuite probes placed 3 depths, low-middle-top, of the stacked hardwood logs. To complete the outdoor pile site, the entire 100×40 ft log stack is overlain with an additional 6-inch spalt starter inoculum and wetted with 250 gallons of water.

The third integral the system and method includes monitoring and correcting spalt incubation conditions using checkpoint metrics to ensure consistent product quality. The chip pile logs are incubated for 12-18 months at ~40% moisture over a temperature range of −5 to 28° C. with supplemental watering when soil moisture sensors record low levels. The logs are inspected and photographed bi-MONTHLY during the months of April-November for the following metrics: wood density changes using a densitometer, bark sheering, aromatic lignin decay activity, pH, temperature, acoustic transformations, wood moisture content, fungal color, presence of mycelial fans, pseudosclerotial plates, rhizomorph or fruiting body formation and zone-line spalt progression. Data is collected at 3 internal inspection passages and additional inspection sites are flagged along the outer edges of the chip pile at intervals of 5 feet.

Indoor Aging Chamber

In another aspect, the system includes a separate moisture and temperature-controlled environment called an 'aging chamber' for inducing indoor spalt lines of ~40 logs or cut lumber stacks when outdoor space and availability of wood chips is limited. This chamber consists of an overhead sliding track door, 22 wide×16 feet tall, a dark (light-limited environment) with 1 access door built onto a radiant heated concrete floor slab with an added 6 inches of A-horizon soil and using a specified combination of fungal isolates, wood chips. The chamber is insulated using closed-cell spray foam polyurethane foam and a 'log-cradle' is buttressed with steel beams for safety. The chamber is ventilated with industrial fans and chilled to 2-13° C. using a medium-temperature range chiller. This chamber can be used for inducing spalted wood from logs or industry standard packets of variable, pre-sewn lumber 4-10 inches wide×10 feet long×1.5" thickness. The flat stacks are arranged within the aging chamber 18 rows tall×48" wide with no space between lumber of irrigated, fungal-inoculated packets that have been wrapped with opaque stretch liner around the outer edges and sides but not on the above-below widest faces of the stacks. Spacers of 4" wood then separate each wrapped-packet on the unwrapped, open-faces and provide airflow and sampling window. Up to 32 packets of wrapped pre-cut hardwood lumber can be stacked this way and vented for CO2 byproduct of fungal decay to remain below 600 ppm using a fan and 18 BTU AC unit.

In an embodiment, the system is implemented to operate at an optimal level using for example, maple wood chips, fungal mix of 3-4 isolates and species, hardwood logs or pre-sewn lumber and will not be at an optimal level if the internal wood pile and/or lumber stack temperatures rise above 18° C., which promotes growth of secondary molds to outcompete the spalting fungal mix. The invention will not work if logs or lumber are allowed to dry out below 30% moisture. In an embodiment, a preferred wood chip source is maple for maintaining populations of spalting fungi. In an example, the diameter and length of logs are about 2 ft to about 3 ft.×10 ft.

Spalt Starter Inoculum Protocol

In an implementation of the system, a spalt starter inoculum protocol may be used having method steps including: 1. Bag Inoculation: Starter cultures of 5 unique spalt fungi in 0.5 gallon grain bags. First, organic wheat (1 kg) that has been rinsed and debrided is simmered in 2 L of water for one hour. After simmering, the cooled grains' moisture content is adjusted to 60% using water. The prepared organic wheat is then carefully placed into a mushroom cultivation bag and sealed with a filter ring and cap. These grain bags are subjected to autoclaving at 15 psi and 121° C. for 60 minutes, followed by a cooling period of 24 hours. Next, five different fungal species are cultivated separately on acidified MEA media, with conditions set at 15° C. for 7 days, and 5° C. for 2 days. Following this, one fully colonized 100 mm petri plate containing spalting fungus is employed to inoculate one of the prepared grain bags. The inoculated grain bags are then placed in an incubation chamber where they undergo cycles of 15° C. for 7 days, and 5° C. for 2 days, all in complete darkness. This incubation process continues for a total of 35 days.

2. Bucket culture: Transfer cultures to maple wood chip substrate in 5-gallon buckets (4:1). First, 4 gallons of maple chips are soaked with water overnight in doubled autoclave bags. After soaking, the water is carefully decanted from the bags. The wood chips are then autoclaved for 2 hours at 15 psi and 121° C. Once autoclaved, the wood chips are left to cool for a period of 24 hours. Next, 5-gallon buckets and their corresponding lids are subjected to surface sterilization using a 1% bleach spray. Following this, the wood chips and two starter cultures are layered alternately into the bucket using gloved hands. A 2-inch air space is intentionally left above the final layer, and the lid is firmly secured in place. The prepared maple wood chip-grain culture is then placed in an incubation environment set at 15° C., where it will remain for a duration of 28 days inside the 5-gallon bucket.

3. Drum bulking: Spalt fungi mix (5) with soil and wood chips in a 55-gallon drum (2:2:1). First, drums and their corresponding lids undergo surface sterilization using a 1% bleach spray, followed by a thorough rinsing with water. Next, the bottom of the drum is prepared by lining it with washed river rocks (3 inches thick), along with water and a hardware mesh. A mixture consisting of fresh soaked maple wood chips (20 gallons) and soil (10 gallons) in a 2:1 ratio is prepared. Additionally, a mixture of spalting fungi from five different bucket cultures, totaling approximately 20 gallons, is combined. The wood chip-soil mix and the spalting fungi mix are then alternately layered into the drum, allowing for some looseness in the arrangement. A 5-inch air space is intentionally left above the final layer, and the lid is securely fastened in place. The culture, comprising soil, wood chips, and spalting fungi, is then placed in an incubation environment set at 15° C. and kept within the 55-gallon drum for a period of 56 days.

4. Bay mix: Climate-controlled bay mix of fresh wood chips and soil with drum culture (9:1:1). First, a mixture of wet maple wood chips (9 cubic yards) and soil (1 cubic yard) in a 9:1 ratio is thoroughly combined using a front loader. Subsequently, four drums (each containing 1 cubic yard) of bulking culture are incorporated into the 9:1 chip-to-soil mixture, again employing a front loader. This resulting 9:1:1 mixture is carefully placed into a climate-controlled curing bay. Inside the curing bay, the soil-wood chip-spalting fungi culture is allowed to incubate at a controlled temperature of 15° C. for a period ranging from 2 to 4 months. Regular monitoring of fungal development is carried out on a monthly basis by sampling for mycelial fans throughout the pile. To promote adequate air circulation, the bay mix is turned over on a monthly basis, utilizing a front loader. Additionally, efforts are made to maintain a relative humidity of 40% through irrigation, and to keep $CO_2$ levels below 600 ppm by means of venting.

5. Final mix: Piles of mill residue: Soil mix are combined with maple wood chips: Bay mix (9:1:1:1). Initially, a 9:1 ratio of mill residue (110 cubic yards) to soil (12 cubic yards) is thoroughly mixed using a front loader. Next, a 1:1 ratio of new maple wood chips (12 cubic yards) and bay mix (12 cubic yards) is blended together. The mill residue-soil mixture is then combined with the new wood chip-bay mix, employing a front loader. This resulting 9:1:1:1 mixture, totaling 146 cubic yards, is shaped into separate conical piles, each reaching a height of 15 feet. Following this, the piles are irrigated with 250 gallons of water and left in an open-air environment for a minimum of one month for conditioning. Monthly monitoring of fungal development is conducted by sampling for mycelial fans throughout the pile. To ensure proper oxygenation, the pile is aerated by mixing with a front loader. Additionally, efforts are made to maintain humidity levels at 40% through irrigation.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order.

Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications can be referenced. The disclosures of these publications in their entirety are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present disclosure is not entitled to antedate such publication by virtue of prior present disclosure. Further, the dates of publication provided herein can be different from the actual publication dates, which can require independent confirmation.

The patentable scope of the present disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Insofar as the description above and the accompanying drawing disclose any additional subject matter that is not within the scope of the claims below, the disclosures are not dedicated to the public and the right to file one or more applications to claims such additional disclosures is reserved.

The foregoing descriptions of specific embodiments of the present invention have been presented for purposes of illustration and description. They are not intended to be exhaustive or to limit the present invention to the precise forms disclosed, and modifications and variations are possible in view of the above teaching. The exemplary embodiment was chosen and described to best explain the principles of the present invention and its practical application, to thereby enable others skilled in the art to best utilize the present invention and its embodiments with modifications as suited to the use contemplated.

It is therefore submitted that the present invention has been shown and described in the most practical and exemplary embodiments. It should be recognized that departures may be made which fall within the scope of the invention. With respect to the description provided herein, it is submitted that the optimal features of the invention include variations in size, materials, shape, form, function and manner of operation, assembly, and use. All structures, functions, and relationships equivalent or essentially equivalent to those disclosed are intended to be encompassed by the present invention.

The following is claimed:

1. A method for producing a spalted wood product, the method comprising:
    applying a wood chip inoculum that comprises a mature fungal component to a wood specimen to produce a fungal-wood mixture;
    aging the fungal-wood mixture at an aging site for an aging period to produce the spalted wood product; and
    wherein the wood chip inoculum further comprises a new wood chip and inoculated woodchip mature spalt inoculum component and a mill residue component, wherein the mill residue component comprises a 3:1 ratio of debarked healthy maple chips to spalted sawdust and/or spalted edge waste and/or spalted bark.

2. The method of claim 1, wherein the wood specimen comprises a basswood specimen, a beech specimen, a poplar specimen, a sugar maple specimen, and/or a yellow birch specimen.

3. The method of claim 1, wherein the wood chip inoculum is produced by:
- inoculating a mature spalt inoculum component with an immature fungal component that comprises a plurality of fungi to produce a mature spalt inoculum-fungal mixture;
- incubating the mature spalt inoculum-fungi mixture, and monitoring fungal development, for about 2-3 months at about 5-15° C. to produce the mature fungal component; and
- combining a mill residue component with the mature fungal component to produce the wood chip inoculum.

4. The method of claim 1, wherein the aging site is prepared by:
- selecting a level site;
- clearing organic 'O' surface soil from the level site;
- removing 'A' horizon soil to a depth of about 1 foot from the level site;
- laying about 6 inches of the wood chip inoculum to the level site;
- stacking the wood specimen over the wood chip inoculum; and
- overlaying the wood specimen with wood chip inoculum.

5. The method of claim 1, further comprising harvesting the wood specimen by:
- winter cutting a plurality of logs from a forest;
- allowing a plurality of forest fungi to colonize on the plurality of logs while in the forest; and
- transporting the plurality of logs from the forest to the aging site.

6. The method of claim 1, further comprising:
- monitoring spalt conditions of the fungal-wood mixture during the aging period; and
- adjusting spalt conditions if necessary to produce the spalted wood product within an aging period.

7. The method of claim 6, wherein spalt conditions include about 40% moisture and a temperature that is less than about 15° C.

8. The method of claim 6, wherein monitoring spalt conditions comprises:
- monitoring mycelial growth and color;
- recording any changes in density of the wood specimen;
- inspecting the fungal-wood mixture for mold contamination;
- measuring moisture content of the fungal-wood mixture;
- testing the fungal-wood mixture for decay and bark sheering; and
- assessing quality or effectiveness of the method for producing the spalted wood product.

9. A method for producing a spalted wood product, the method comprising:
- preparing a wood chip inoculum by:
  - inoculating a mature spalt inoculum component with an immature fungal component that comprises a plurality of fungi to produce a mature spalt inoculum-fungal mixture;
  - incubating the mature spalt inoculum-fungi mixture, and monitoring fungal development, for about 2-3 months at about 5-15° C. to produce the mature fungal component;
  - combining a mill residue component with the mature fungal component to produce the wood chip inoculum;
- applying the prepared wood chip inoculum that comprises a mature fungal component to a wood specimen to produce a fungal-wood mixture; and
- aging the fungal-wood mixture at an aging site for an aging period to produce the spalted wood product.

10. A method for producing a spalted wood product, the method comprising:
- applying a wood chip inoculum that comprises a mature fungal component to a wood specimen to produce a fungal-wood mixture;
- aging the fungal-wood mixture at an aging site for an aging period to produce the spalted wood product; and
  - wherein monitoring spalt conditions comprises:
    - monitoring mycelial growth and color;
    - recording any changes in density of the wood specimen;
    - inspecting the fungal-wood mixture for mold contamination;
    - measuring moisture content of the fungal-wood mixture;
    - testing the fungal-wood mixture for decay and bark sheering; and
    - assessing quality or effectiveness of the method for producing the spalted wood product.

* * * * *